United States Patent
Horn et al.

(10) Patent No.: US 9,528,977 B2
(45) Date of Patent: *Dec. 27, 2016

(54) SIMPLIFIED STORAGE OF AT LEAST ONE TEST ELEMENT INCLUDING A DRY REAGENT LAYER HAVING AN ENZYME AND A STABILIZED COENZYME

(75) Inventors: Carina Horn, Biblis (DE); Christian Freitag, Weinolsheim (DE); Hans-Peter Haar, Wiesloch (DE); Heino Eikmeier, Lorsch (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/400,267

(22) Filed: Feb. 20, 2012

(65) Prior Publication Data

US 2012/0241335 A1    Sep. 27, 2012

Related U.S. Application Data

(63) Continuation of application No. PCT/EP2010/062179, filed on Aug. 20, 2010.

(30) Foreign Application Priority Data

Aug. 20, 2009  (EP) .................................. 09168331

(51) Int. Cl.
  *G01N 33/487*  (2006.01)
  *G01N 33/32*   (2006.01)
  *G01N 27/327*  (2006.01)

(52) U.S. Cl.
  CPC .... *G01N 33/48778* (2013.01); *G01N 27/3272* (2013.01); *G01N 33/48757* (2013.01); *G01N 33/48764* (2013.01)

(58) Field of Classification Search
  None
  See application file for complete search history.

(56) References Cited

U.S. PATENT DOCUMENTS 5,183,742 A * 2/1993 Omoto et al. .................. 435/14
5,720,924 A * 2/1998 Eikmeier et al. ............. 422/550
(Continued)

FOREIGN PATENT DOCUMENTS

CN    1833610    9/2006
CN    1985167    6/2007
(Continued)

OTHER PUBLICATIONS

International Search Report; PCT/EP2010/062179.
(Continued)

*Primary Examiner* — Erik B Crawford
*Assistant Examiner* — Gary E Hollinden

(57) ABSTRACT

Storage containers for storing at least one diagnostic test element including an enzyme and a stabilized coenzyme are disclosed. In addition, diagnostic products which include diagnostic test elements including an enzyme and a stabilized coenzyme, as well as analytical measuring devices which include such storage containers or diagnostic products, are also disclosed. Other aspects include, but are not limited to, unique methods, techniques, products, systems and devices involving test elements which include an enzyme and a stabilized coenzyme.

22 Claims, 23 Drawing Sheets

(56) References Cited

U.S. PATENT DOCUMENTS

| | | | |
|---|---|---|---|
| 5,788,064 A * | 8/1998 | Sacherer et al. | 206/204 |
| 5,801,006 A * | 9/1998 | Kaufman | 435/15 |
| 7,553,615 B2 | 6/2009 | Heindl et al. | |
| 7,998,407 B2 * | 8/2011 | Wohland | 422/404 |
| 8,153,080 B2 | 4/2012 | Kheiri et al. | |
| 8,394,328 B2 * | 3/2013 | Neel et al. | 422/82.05 |
| 8,783,102 B2 * | 7/2014 | Heck et al. | 73/431 |
| 2002/0022246 A1 * | 2/2002 | Lin et al. | 435/31 |
| 2003/0175993 A1 * | 9/2003 | Toranto et al. | 436/518 |
| 2003/0186446 A1 * | 10/2003 | Pugh | 436/46 |
| 2004/0258564 A1 | 12/2004 | Charlton | |
| 2006/0240403 A1 * | 10/2006 | List et al. | 435/4 |
| 2007/0026476 A1 * | 2/2007 | Heindl et al. | 435/14 |
| 2008/0131322 A1 * | 6/2008 | Kheiri et al. | 422/82.01 |
| 2008/0213809 A1 * | 9/2008 | Heindl et al. | 435/14 |
| 2011/0229960 A1 | 9/2011 | List et al. | |
| 2012/0041339 A1 | 2/2012 | Kuhr et al. | |
| 2012/0241335 A1 | 9/2012 | Horn et al. | |
| 2012/0252135 A1 * | 10/2012 | Babic et al. | 436/178 |
| 2013/0011871 A1 * | 1/2013 | Horn et al. | 435/26 |

FOREIGN PATENT DOCUMENTS

| | | | |
|---|---|---|---|
| DE | 10 2005 013 685 A1 | 9/2006 | |
| EP | 0 951 939 A2 | 4/1999 | |
| EP | 1 022 565 A2 | 1/2000 | |
| EP | 1 736 772 A1 | 6/2005 | |
| EP | 1 702 565 A2 | 9/2006 | |
| EP | 1 801 584 A1 | 6/2007 | |
| EP | 1723412 B1 | 2/2008 | |
| EP | 1 914 547 A1 | 4/2008 | |
| EP | 2467717 B1 | 12/2014 | |
| GB | 1341606 * | 12/1973 | G01N 31/14 |
| JP | 2001-264332 | 9/2001 | |
| JP | 2006-511264 | 4/2006 | |
| JP | 2006-263465 | 10/2006 | |
| JP | 2015103622 A | 6/2015 | |
| WO | WO 98/33936 | 8/1998 | |
| WO | WO 01/49247 A2 | 7/2001 | |
| WO | WO 2004/047642 | 6/2004 | |
| WO | WO 2004/056269 A1 | 7/2004 | |
| WO | WO 2005/084530 A2 | 9/2005 | |
| WO | WO 2005/104948 A1 | 11/2005 | |
| WO | WO 2006/002432 A1 | 1/2006 | |
| WO | WO 2007/012494 A1 | 1/2007 | |
| WO | WO 2009/135035 * | 11/2009 | C07H 19/207 |
| WO | WO 2010/094427 A2 | 8/2010 | |

OTHER PUBLICATIONS

Mariarita Bertold et al., Folding pathway of the pyridoxal 5'-phosphate C-S lyase MalY from *Escherichia coli*, Biochem. J., 2005, pp. 885-898, vol. 389, Copyright 2005 Biochemical Society.

Robert H. H. Van Den Heuvel et al., Enzyme Catalysis and Regulation: Coenzyme Binding during Catalysis Is Beneficial for the Stability of 4-Hydroxyacetophenone Monooxygenase, The Journal of Biological Chemistry, Sep. 16, 2005, pp. 32115-32121, vol. 280 No. 37.

Kuan Pan et al., Thermodynamics of Lanthanum Fluoride in Aqueous Sodium Perchlorate, Journal of Chinese Chemical Society, Mar. 1974, vol. 21 Issue 1, Copyright 1974 The Chemical Society Located in Taipei & Wiley-VCH Verlag GmbH & Co. KGaA, Weinheim, Germany.

Does Coenzyme Binding Determine Enzyme Stability?, Nutrition Reviews, Aug. 1978, 2 pages, vol. 36 Issue 8, Copyright 1978 International Life Sciences Institute.

James T. Slama et al., Carbanicotinamide Adenine Dinucleotide: Synthesis and Enzymological Properties of a Carbocyclic Analogue of Oxidized Nicotinamide Adenine Dinucleotide, Biochemistry, 1988, pp. 183-193, vol. 27 No. 1, Copyright 1988 American Chemical Society.

James T. Slama et al., Inhibition of NAD Glycohydrolase and ADP-ribosyl Transferases by Carbocyclic Analogues of Oxidized Nicotinamide Adenine Dinucleotide, Biochemistry, 1989, pp. 7688-7694, vol. 28 No. 19, XP-002502968, Copyright 1989 American Chemical Society.

Edward J. Hutchinson et al., Synthesis of carbocyclic NAD+ containing a methylenebisphosphonate linkage for the investigation of ADP-ribosyl cyclase, Chemical Communications, 1996, pp. 2765-2766.

Johannes Everse et al., The Pyridine Nucleotide Coenzymes, 1982, 12 pages, Copyright 1982 Academic Press, Inc., New York, NY.

* cited by examiner test strips plastic box containing desiccant

SIMPLIFIED STORAGE OF AT LEAST ONE TEST ELEMENT INCLUDING A DRY REAGENT LAYER HAVING AN ENZYME AND A STABILIZED COENZYME

CROSS-REFERENCE TO RELATED APPLICATIONS

This application is a continuation of International Application No. PCT/EP2010/062179 filed Aug. 20, 2010, which claims priority to European Patent Application No. 09168331.8 filed Aug. 20, 2009. Each of the referenced applications is incorporated herein by reference in its entirety.

FIELD OF THE INVENTION

The present application concerns storage containers for storing at least one diagnostic test element which includes an enzyme and a stabilized coenzyme. Additionally or alternatively, the present application concerns diagnostic products which include the above-described diagnostic test elements, as well as analytical measuring devices which include such storage containers or diagnostic products.

BACKGROUND

Diagnostic test elements are important components of clinically relevant analytical methods. In this connection, the focus is on the measurement of analytes, for example metabolites or substrates, which for example can be determined directly or indirectly with the aid of an enzyme that is specific for the analyte. In this case, the analytes are converted with the aid of an enzyme-coenzyme complex and subsequently quantified. This entails the analyte to be determined being brought into contact with a suitable enzyme, a coenzyme and optionally a mediator, whereby the coenzyme is physicochemically changed, for example oxidized or reduced, by the enzymatic reaction. If a mediator is additionally used, it usually transfers electrons from the reduced coenzyme released during the conversion of the analyte onto an optical indicator or the conductive components of an electrode so that the process can be detected, by way of non-limiting example, photometrically or electrochemically. A calibration provides a direct relationship between the measured value and the concentration of the analyte to be determined.

An important criterion when providing diagnostic test elements is their long-term stability. Certain test elements known from the prior art which are used in the determination of blood glucose are generally very sensitive to moisture and heat, such that upon exposure to the same the function of the coenzyme and mediator, for example, is usually impaired. In certain instances where, for example, tests are carried out by the end user himself, erroneous results can therefore occur due to an incorrect, unnoticed faulty storage of the measurement system which can be hardly detected by the user and may result in incorrect treatment of the respective disease.

Thus, special protective measures are required for the production and storage of conventional diagnostic test elements which prevent contact of the test chemistry of the diagnostic test element with moisture and heat, and in particular with moisture. This can be accomplished by, for example, introducing desiccants, such as silica gel or a molecular sieve, or sealing elements into a storage container containing the test element.

Consequently, such test elements have the disadvantage that they have to be used within a few minutes after removal from the storage container in order to ensure faultless functionality. If it is intended to insert the test element into an analytical measuring device after it has been removed from the storage container or from a primary packaging, the test element must additionally be kept dry until it has been completely used up which requires elaborate apparatus and considerably limits the design of the test element as well as of the analytical measuring device.

One non-limiting object of the present application is to provide a storage container for diagnostic test elements in which the disadvantages of the prior art are at least partially eliminated. In one particular but non-limiting aspect, the ability to store the diagnostic test element in the storage container without elaborate apparatus and over a long period of time in the presence of moisture and/or heat without thereby suffering a significant loss of enzyme activity is desired.

SUMMARY

In one non-limiting aspect, storage containers for storing at least one diagnostic test element including an enzyme and a stabilized coenzyme are provided. Still, other aspects include, but are not limited to, diagnostic products which include diagnostic test elements including an enzyme and a stabilized coenzyme, as well as analytical measuring devices which include such storage containers or diagnostic products.

In one embodiment, a storage container includes at least one diagnostic test element including an enzyme and a stabilized coenzyme. In addition, the storage container is essentially free of at least one of desiccants and sealing elements which substantially prevent the penetration of moisture from the environment into the storage container.

In another embodiment, a storage container includes at least one diagnostic test element including an enzyme, a stabilized coenzyme and one or more test areas. Further, the storage container enables an exchange of moisture between one or more unused test areas and one or more used test areas of the at least one test element, and the one or more unused test areas and the one or more used test areas are stored in a single chamber or in two chambers separated from one another by a moisture-permeable dividing wall.

In yet another embodiment, a diagnostic product includes a plurality of interconnected, individually separable test strips in at least one of a bar-shaped and a roll-shaped arrangement, and each of the test strips includes an enzyme and a stabilized coenzyme.

Still, in another embodiment, an analytical measuring device includes one of the above-described storage containers or the above-described diagnostic product.

Other aspects include, but are not limited to, unique methods, techniques, products, systems and devices involving test elements which include an enzyme and a stabilized coenzyme.

Further embodiments, forms, objects, features, advantages, aspects, and benefits shall become apparent from the following description and drawings.

DETAILED DESCRIPTION

Figure 1:
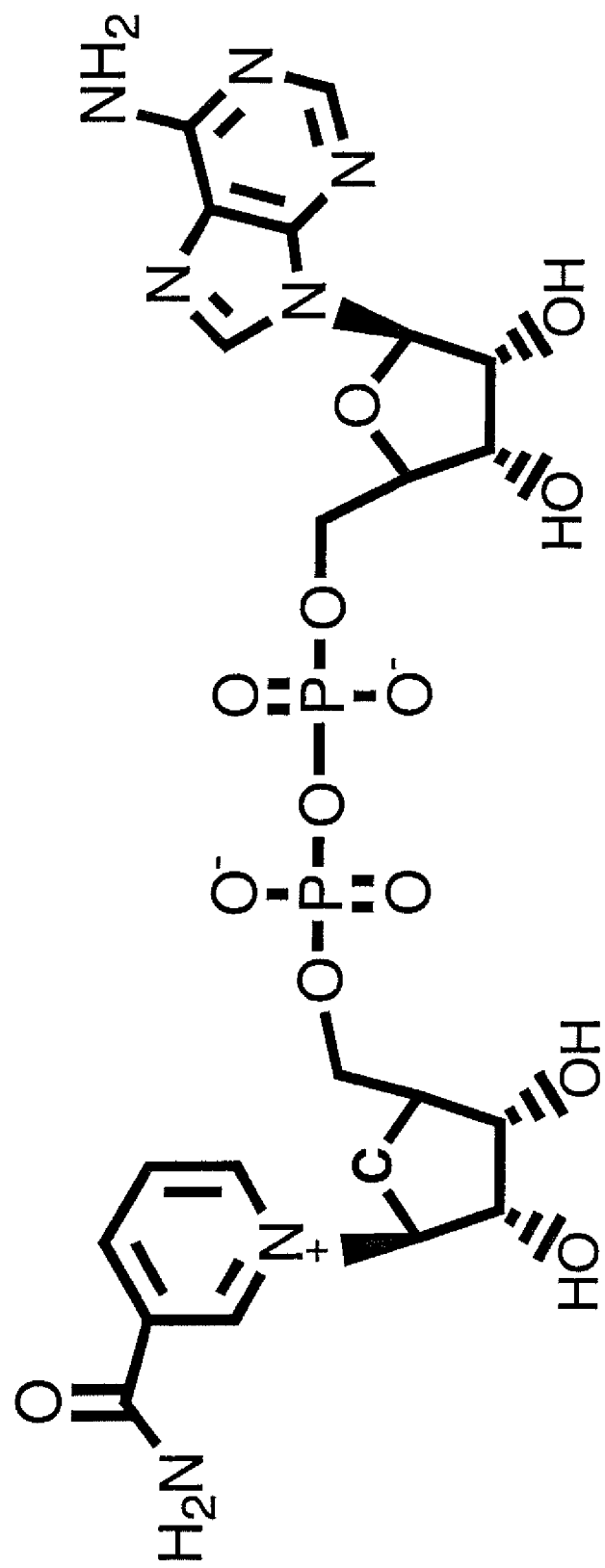
FIG. 1 illustrates the formula of the stable coenzyme carbaNAD (cNAD).

In one non-limiting aspect, storage containers for storing at least one diagnostic test element including an enzyme and a stabilized coenzyme are provided. Still, other aspects include, but are not limited to, diagnostic products which include diagnostic test elements including an enzyme and a stabilized coenzyme, as well as analytical measuring devices which include such storage containers or diagnostic products.

In one embodiment, a storage container contains at least one diagnostic test element including an enzyme and a stabilized coenzyme, and the storage container is essentially free of desiccants and/or includes no sealing elements which substantially prevent the penetration of moisture from the environment into the storage container.

In another embodiment, a storage container contains at least one diagnostic test element which includes an enzyme and a stabilized coenzyme, and the storage container enables moisture to be exchanged between one or more unused test areas and one or more used test areas of the test element or of the test elements.

It has been surprisingly discovered that diagnostic test elements which include an enzyme and a stabilized coenzyme in their chemical coating are not subject to a significant decrease of enzyme activity, even at an elevated relative air humidity and/or at elevated temperatures over several weeks or months, which thus allows a reduction in the complexity of the apparatus required to prevent penetration of moisture into a storage container containing the test element. This at the same time enables a simpler and more reliable handling of the diagnostic test element by the user.

The above-described finding is surprising because, amongst other reasons, it was previously known that while enzymes in the presence of the native coenzyme have an increased short-term stability of several hours (Bertoldi et al., Biochem. J. (2005), 389, 885; van den Heuvel et al., J. Biol. Chem. (2005), 280, 32115; and Pan et al., J. Chin. Biochem. Soc. (1974), 3, 1), they have a lower stability over a longer period (Nutrition Reviews (1978), 36, 251). The long-term stability towards moisture and/or heat that has now been observed of diagnostic test elements which include an enzyme and a stabilized coenzyme is all the more surprising because stabilized coenzymes have a lower binding constant with the enzyme than the corresponding native coenzymes.

As used herein, the term "storage container" refers to a container which can be inserted into an analytical measuring device and is designed such that one individual test area of at least one diagnostic test element, which can include a single test area or several test areas, stored in the container can at any one time interact with the analytical measuring device. The interaction between the test area of the diagnostic test element and the analytical measuring device can in principle take place in any manner. In one particular form, the interaction takes place in an optical manner such as, for example, by irradiating the test area wetted with a sample of the analyte with light of a suitable wavelength and subsequently detecting the radiation emitted from the test area by means of the analytical measuring device.

In order to enable a qualitative and/or quantitative determination of the analyte using an analytical measuring device, the storage containers disclosed herein include a sample application position in which a test area of the diagnostic test element stored in the storage container can be brought into contact with a sample of the analyte, a measuring position in which the analyte can be determined by interaction of a test area of the diagnostic test element and the analytical measuring device, as well as at least one storage position in which the test area of the diagnostic test element can be stored before and/or after contact with the sample and subsequent determination of the analyte.

The storage containers described herein may include any physical form which is familiar to a person skilled in the art and appears suitable for the purposes disclosed herein, provided that they allow the accommodation of at least one diagnostic test element, and in particular but non-limiting forms, a tape magazine or test strip magazine. The storage containers can have, for example, a round, rounded or angular configuration where a particularly high tightness can be achieved by using round or rounded storage containers. Since the diagnostic test elements disclosed herein have a very stable test chemistry, an extremely high tightness is, however, not absolutely necessary and thus readily allows the implementation of an angular design of the storage containers.

Specific but non-limiting examples of storage containers include, among others, pouches, boxes, cans, simple dispensers as well as bags. In one aspect, one or more of these storage containers may contain a plurality of individual diagnostic test elements such as, for example, a plurality of diagnostic test elements that are joined together but can be individually separated and can in turn be accommodated together with further storage containers disclosed herein in a suitable outer packaging for the purpose of transport. The term "plurality" as used in the present application refers to any number >1.

In order to prevent the entry of dust particles or other particulate materials that could impair the determination of the analyte from the outer environment into their interior, the storage containers disclosed herein only have entry openings with a diameter of ≤100 µm. In one particular form, the entry openings have a diameter of ≤20 µm. The term "entry opening" as used in the present application encompasses any opening through which particles of an inorganic and/or organic material can penetrate from the outer environment of the storage containers into their interior such as, for example, the pores of the material used to produce the storage containers.

The storage containers disclosed herein may consist of any material which appears suitable to a person skilled in the art for the purposes of storing diagnostic test elements. However, in one aspect the storage containers consist at least partially, i.e. partially or completely, of at least one material permeable to water vapour which can optionally additionally include additives such as, for example, dyes, smoothing substances, aging inhibitors and/or UV inhibitors. Edible paper, coated foils, wood, plastic, paper, cardboard, parchment, pressboard or plywood can be used as the material that is permeable to water vapour. In one particular form, the material that is permeable to water vapour is plastic. In another particular form, a storage container includes a plastic selected from the group of polyamide, polycarbonate, polyester, polyethylene and polypropylene as the material that is permeable to water vapour.

In forms where a tape magazine is used as the storage container, it may include a single diagnostic test element where the diagnostic test element in turn usually includes more than one test area. In further aspects of this form, the test element includes at least 10, at least 25 or at least 50 individual test areas. If a test strip magazine is used as the storage container, then it may include at least 3, at least 5, or at least 7 diagnostic test elements, where the diagnostic test elements in this case usually have only a single test area but if required can have more than one test area.

The storage containers disclosed herein may also include one or more spatially separated areas for storing the at least one diagnostic test element. If the diagnostic test element includes more than one test area which can be brought into contact with a sample containing the analyte, then the storage container may include one or two areas that are spatially separated from one another such as, for example, one or two chambers in which the test areas of the diagnostic test element can be stored.

If the storage container includes two areas spatially separated from one another for storing the diagnostic test element, then one area can, for example, be used to store unused test areas of a diagnostic test element whereas the second area is provided to store used test areas of the diagnostic test element. This ensures that unused test areas and used test areas of the diagnostic test element cannot come into direct contact with one another within the storage container. It is also possible for each diagnostic test element to be stored before or after use in its own area such as, for example, in its own chamber.

In the case of storage containers which only include one area such as, for example, a single chamber for storing a diagnostic test element with more than one test area, unused test areas as well as used test areas of the diagnostic test element are stored in the one area. In the absence of a second chamber or physical means, such as, for example a dividing wall, that prevent contact between unused test areas and used test areas within the storage container, it is possible to considerably simplify the production of the storage containers as well as the storage of the test elements which makes the process more economical. The term "unused test area" as used in the present application refers to a test area of a diagnostic test element described in the present application before contact of the test area with a sample of an analyte to be determined; in contrast, the term "used test area" is used to refer to a test area after contact of the test area with a sample of the analyte to be determined.

In one particular embodiment, the storage containers disclosed herein are tape magazines or test strip magazines. Tape magazines which have two chambers for the separate storage of unused test areas and used test areas of a diagnostic test element present in the form of a test tape are described for example in German Patent Publication No. DE 10 2005 013 685 A1, European Patent Publication No. EP 1 739 432 A1 and International Patent Publication No. WO 2004/047642 A1. Test strip magazines are generally known to a person skilled in the art and include, but are not limited to, blister magazines, leporello magazines, disk magazines, stack magazines, drum magazines and turning magazines that are described, for example, in European Patent Publication No. EP 0 951 939 A2, European Patent Publication No. EP 1 022 565 A2, European Patent Publication No. EP 1 736 772 A1, International Patent Publication No. WO 2005/104948 A1 and International Patent Application No. PCT/EP2010/000865, the disclosures of which, especially with regard to the geometry of the storage containers, are incorporated herein by reference in their entirety.

In one embodiment, a storage container is essentially free of desiccants. In this connection, the term "essentially free of desiccants" means that the storage container contains an amount of <5% by weight, an amount of <1% by weight, an amount of <0.1% by weight, an amount of <0.01% by weight or an amount of <0.001% by weight desiccant based on the empty weight of the storage container. The possibility of significantly reducing the amount of desiccant or of completely omitting desiccants within the scope of producing and storing the diagnostic test elements described herein has the advantage that the production as well as the storage of the test elements can be simplified and thus made more economical.

If the storage container disclosed herein is not completely free of desiccants, i.e. it contains a desiccant in one of the amounts stated above, the desiccant can be brought separately into the storage container or/and integrated separately into the housing of the storage container. If the storage container contains the desiccant integrated into its housing, this means that the desiccant is incorporated into the solid housing of the storage container and enables at least one inner surface of the storage container to absorb moisture from the interior of the storage container. Such storage containers can, for example, be produced by injecting the desiccant into a mould used to produce the housing and subsequently to cool/harden the plastic composition.

In one form of this embodiment, the storage container contains no sealing elements which substantially prevent the penetration of moisture from the environment into the storage container. The term "sealing elements which substantially prevent the penetration of moisture from the environment into the storage container" means that the sealing elements completely prevent the penetration of moisture from the environment into the storage container or only allow the penetration of an amount of moisture which results in no impairment of the test chemistry of the diagnostic test element for example due to inactivation of the coenzyme, and where applicable the mediator, over a period of at least 4 weeks, at least 8 weeks or at least 12 weeks.

Non-limiting examples of sealing elements in the sense of the present application include seals and tight sealings. Sealing elements which allow moisture to penetrate from the environment into the storage containers described herein and can be used in one particular embodiment are thus mainly used to protect the diagnostic test elements stored in the storage container from dust particles or mechanical damage and can, for example, be made of paper, parchment or other materials familiar to a person skilled in the art. Stable metal foils which are usually used to seal storage containers with diagnostic test elements contained therein can thus be avoided in an efficient and cost-saving manner.

The omission of sealing elements which substantially prevent the penetration of moisture from the environment into the storage container can, amongst other things, considerably simplify and economize the production and storage of the test elements described herein. Thus, the omission of mechanical components on the one hand, leads to a considerable reduction of the construction volume compared to conventional storage containers. On the other hand, the omission of sealing elements also considerably reduces the pulling forces which are, for example, required in the case of tape magazines with a sealing element to transport unused test areas of a diagnostic test element present in the form of a test tape from a storage position within the tape magazine to a sample application position or measuring position outside the tape magazine due to the mechanical resistance caused by the sealing element.

In this respect, one embodiment of the storage containers disclosed herein provides that the minimum and/or maximum pulling force required to transport unused test areas of a diagnostic test element from a storage position within the storage container to a sample application position and/or measuring position outside the storage container, and/or that required to transport used test areas of the diagnostic test element from a sample application position and/or measuring position outside the storage container to a storage position within the storage container, is reduced compared to a corresponding storage container with a sealing element. In this case, the reduction of the minimum and/or maximum pulling force is usually at least 10%, at least 25% or at least 50% based on the minimum and/or maximum pulling force required in a corresponding storage container with a sealing element.

Reduction of the minimum and/or maximum pulling force required to further transport the test areas of a diagnostic test element in a storage container disclosed herein can, for example, reduce the energy required for the further transport of a test tape in the case of tape magazines, which leads to an overall reduction in the energy requirement of an analytical measuring device including the storage container and thus, for example, allows the use of smaller batteries or a lower number of batteries. This in turn leads to smaller constructed sizes so that overall the size of the storage containers can be significantly reduced and the materials required to produce the storage container can similarly be reduced.

In a further embodiment, a storage container allows moisture exchange between unused test areas and used test areas of an individual diagnostic test element or of several diagnostic test elements. In one aspect, diagnostic test elements may be used in such storage containers which include more than only one test area for determining an analyte such as, for example, test tapes.

In one form of this embodiment, the storage of unused test areas and used test areas of a diagnostic test element described in the present application can take place in any manner provided that an exchange of moisture is possible between the unused test areas and the used test areas. Thus, unused test areas and used test areas can, for example, be stored in a storage container which includes one or more storage areas, and in particular but non-limiting forms, the storage container includes one, two or more than two chambers.

In the storage container of this embodiment the unused test areas and the used test areas of the diagnostic test element may be stored in a single chamber or in two chambers separated from one another by a moisture-permeable dividing wall. If unused test areas and used test areas are accommodated in a single chamber, the unused test areas and the used test areas may be arranged within the one chamber in such a manner that moisture can be exchanged between unused test areas and used test areas but with no direct contact between unused test areas and used test areas of the diagnostic test element to avoid contamination of unused test areas. Due to the simplified design of the storage container it can in turn be miniaturized, produced in a simpler manner and provided more cost-effectively.

While not previously discussed, it should be understood that the storage containers described herein can also include any combination of the embodiments described above. Similarly, a further embodiment is directed towards a storage container containing at least one diagnostic test element which includes an enzyme and a stabilized coenzyme where the storage container (a) is essentially free of desiccants, (b) comprises no sealing elements which substantially prevent penetration of moisture from the environment into the storage container and/or (c) enables moisture to be exchanged between unused test areas and used test areas of the test element or test elements.

Furthermore, the storage containers described herein can, however, also include physical means which prevent the penetration of particulate substances from the environment into the storage container but in contrast allow the penetration of moisture. In this connection, in the case of diagnostic test elements having more than one test area such as, for example, a test tape, the further transport of test areas in the storage container may not be impaired by an increase in the minimum and/or maximum pulling force required for the further transport of the test areas in the storage container, compared to a storage container without the corresponding physical means, for example as described above.

In one particular form, the storage containers described herein contain at least one diagnostic test element. Diagnostic test elements which can be used within the scope of the present application generally include any test element known to a person skilled in the art which is suitable for determining an analyte and can be stored in a storage container disclosed herein. The term "storage" means in this connection that the diagnostic test element is accommodated in the storage container for a period of at least two weeks, at least three months, at least six months or at least twelve months where the storage takes place at atmospheric pressure, room temperature (25° C.) and a relative air humidity of at least 50%.

In one form, the diagnostic test elements disclosed herein are of the form on which the analyte can be applied in the form of an aqueous or non-aqueous solution. In one particular embodiment, the test element is in this case a test tape, a test disk, a test pad, a test strip or the diagnostic elements mentioned in International Patent Publication No. WO 2005/084530 A2, the contents of which are incorporated herein by reference in their entirety. If the storage containers described in the present application are designed as a test strip magazine, they may include a plurality of interconnected and individually separable test strips in a bar-shaped and/or roll-shaped arrangement. If desired, the diagnostic test elements can additionally include a mark such as, for example, a barcode which if required enables a subsequent identification of the test element used in each case.

The term "test tape" as used herein refers to a tape-like test element which usually comprises more than a single test area. In one aspect, the tape-like test element includes at least 10 individual test areas, at least 25 individual test areas or at least 50 individual test areas. In one embodiment, the individual test areas are each arranged at a distance of a few millimeters to a few centimeters from one another such as, for example, at a distance of <2.5 cm. The test tape can optionally include marker areas between consecutive test areas to detect the distance travelled during tape transport and/or for calibration and is usually not coated with a test chemistry. Test tapes with marker areas to detect the distance travelled during tape transport between successive test areas are described, for example, in European Patent Publication No. EP 1 739 432 A1, the disclosure of which is hereby incorporated herein by reference in its entirety.

The test tape described above may be a continuous test tape on which at least two test areas are arranged directly next to one another; i.e. without a gap between the two test areas. Such an arrangement of test areas has the advantage that a larger number of test areas can be positioned on the test tape, and it also enables moisture to be exchanged between the individual test areas. This allows the production of test tapes to be simplified and made more cost-effective.

In the case of a continuous test tape, it is possible, for example, to arrange all test areas with the exception of the first and last test areas in such a manner that both sides of an individual test area directly adjoin another test area. Alternatively, in the case of a continuous test tape it is also possible to arrange several test areas, for example 5 test areas or more, directly next to one another where consecutive groups of test areas are in turn arranged at a distance of a few millimeters up to a few centimeters from one another at, for example, a distance of <2.5 cm. In this case, the test tape can optionally also have marker areas to detect the distance travelled during tape transport and/or for calibration between consecutive groups of test areas.

The term "test disk" as used herein refers to a disk-shaped test element which can include one or more individual test areas such as, for example, at least 10 individual test areas. In one embodiment, the test disk is coated with a thin layer of the test chemistry, for example with a layer having a thickness of about 20 µm, onto which a sample of the analyte can be applied whereby an area of the test disk of greater or lesser size is wetted by the sample depending on the volume of the sample and can be used to determine the analyte. The non-wetted area of the test disk which can be partially or completely moistened due to the passage of moisture through the test chemistry layer is subsequently available for further determinations of the analyte.

The enzyme used in the diagnostic test elements described herein can be any enzyme which appears suitable to a person skilled in the art for the purposes of the respective application of the test element. In one non-limiting form, the enzyme is a dehydrogenase. In another form, the enzyme is a nicotinamide adenine dinucleotide (NAD/NADH)-dependent or nicotinamide adenine dinucleotide phosphate (NADP/NADPH)-dependent dehydrogenase selected from an alcohol dehydrogenase (EC 1.1.1.1; EC 1.1.1.2), an L-amino acid dehydrogenase (EC 1.4.1.5) a glucose dehydrogenase (EC 1.1.1.47), a glucose-6-phosphate dehydrogenase (EC 1.1.1.49), a glycerol dehydrogenase (EC 1.1.1.6), a 3-hydroxy-butyrate dehydrogenase (EC 1.1.1.30), a lactate dehydrogenase (EC 1.1.1.27; 1.1.1.28), a malate dehydrogenase (EC 1.1.1.37) and a sorbitol dehydrogenase. In one particular embodiment, the enzyme is a glucose dehydrogenase (EC 1.1.1.47) or a glucose-6-phoshate dehydrogenase (EC 1.1.1.49).

A stabilized coenzyme in the sense of the present application is a coenzyme which has been chemically modified compared to the native coenzyme and which at atmospheric pressure has a higher stability towards moisture, temperatures, in particular those in the range of 0° C. to 50° C., acids and bases, in particular those in the range of pH 4 to pH 10, and/or nucleophiles such as, for example, alcohols or amines compared to the native coenzyme. Similarly, it should be understood that the stabilized coenzyme can display its effect under identical environmental conditions over a longer period than the native coenzyme. In one form, the stabilized coenzyme has a higher hydrolytic stability compared to the native coenzyme. In another particular form, the stabilized coenzyme has a complete resistance to hydrolysis under the test conditions compared to the native coenzyme. In comparison with the native coenzyme, the stabilized coenzyme can have a reduced binding constant for the enzyme such as, for example, a binding constant reduced by a factor of two or more.

More particular but non-limiting examples of stabilized coenzymes include stabilized NAD(P)/NAD(P)H compounds; i.e. chemical derivatives of native nicotinamide adenine dinucleotide (NAD/NADH) or nicotinamide adenine dinucleotide phosphate (NADP/NADPH). In one form, the stabilized NAD(P)/NAD(P)H compounds may include a 3-pyridinecarbonyl or a 3-pyridinethiocarbonyl residue which is linked without a glycosidic bond via a linear or cyclic organic residue, and in particular but not exclusively via a cyclic organic residue to a phosphorus-containing residue such as a phosphate residue.

In one particular form, the stabilized NAD(P)/NAD(P)H compound is selected from compounds of the general formula (I):

(I)

in which
A=adenine or an analogue thereof;
T=in each case independently denotes O or S;
U=in each case independently denotes OH, SH, $BH_3^-$, or $BCNH_2^-$;
V=in each case independently denotes OH or a phosphate group, or two groups which form a cyclic phosphate group;
W=COOR, $CON(R)_2$, COR, or $CSN(R)_2$ in which R in each case independently denotes H or a $C_1$-$C_2$ alkyl;
$X^1$, $X^2$=in each case independently denote O, $CH_2$, $CHCH_3$, $C(CH_3)_2$, NH, or $NCH_3$;
Y=NH, S, O, or $CH_2$;
Z=a linear or cyclic organic residue;
provided that Z and the pyridine residue are not linked by a glycosidic bond, or a salt or optionally a reduced form thereof.

In certain forms, Z in the compounds of formula (I) is a linear residue with 4-6 C atoms, and in one particular form with 4 C atoms, in which 1 or 2 C atoms are optionally replaced by one or more heteroatoms selected from O, S and N, or a residue comprising a cyclic group with 5 or 6 C atoms which optionally contains a heteroatom selected from O, S and N as well as optionally one or more substituents, and a residue $CR^4_2$, where $CR^4_2$ is bound to the cyclic group and to $X^2$, where $R^4$ is in each case independently denotes H, F, Cl, or $CH_3$.

In one particular form, Z is a saturated or unsaturated carbocyclic or heterocyclic 5-membered ring and more particularly but not exclusively is a compound of the general formula (II)

(II)

in which a single or double bond may be present between $R^{5'}$ and $R^{5''}$, where
$R^4$=in each case independently denotes H, F, Cl, $CH_3$;
$R^5$=$CR^4_2$;
$R^{5'}$=O, S, NH, $NC_1$-$C_2$-alkyl, $CR^4_2$, CHOH, or $CHOCH_3$, and $R^{5''}$=$CR^4_2$, CHOH, or $CHOCH_3$ if there is a single bond between $R^{5'}$ and $R^{5''}$;
$R^{5'}$=$R^{5''}$=$CR^4$ if there is a double bond between $R^{5'}$ and $R^{5''}$; and
$R^6$, $R^{6'}$=in each case independently denote CH or $CCH_3$.

In one embodiment, the compounds disclosed herein contain adenine or adenine analogues such as, for example, $C_8$-substituted and $N_6$-substituted adenine, deaza variants such as 7-deaza, aza variants such as 8-aza or combinations such as 7-deaza or 8-aza or carbocyclic analogues such as formycin where the 7-deaza variants can be substituted in the 7 position by halogen, $C_{1-6}$ alkinyl, $C_{1-6}$ alkenyl, or $C_{1-6}$ alkyl.

In a further embodiment, the compounds contain adenosine analogues which contain, for example, 2-methoxydeoxyribose, 2'-fluorodeoxyribose, hexitol, altritol or polycyclic analogues such as bicyclo, LNA and tricyclo sugars instead of ribose.

In particular forms (di)-phosphate oxygens can also be isotronically replaced in the compounds of formula (I) such as, for example, $O^-$ by $S^-$ or $BH_3^-$, O by NH, $NCH_3$ or $CH_2$ and =O by =S. In particular but non-limiting forms, W in the compounds of formula (I) described herein is $CONH_2$ or $COCH_3$.

In one form, $R^5$ in the groups of formula (II) is $CH_2$. Furthermore, in one form $R^{5'}$ is selected from $CH_2$, CHOH and NH. In a particular embodiment, $R^{5'}$ and $R^{5''}$ are each CHOH. In yet another particular embodiment, $R^{5'}$ is NH and $R^{5''}$ is $CH_2$. One specific embodiment includes a compound of formula (II) in which $R^4$=H, $R^5$=$CH_2$, $R^{5'}$=$R^{5''}$=CHOH and $R^6$=$R^{6'}$=CH.

In one particular embodiment, the stabilized coenzyme is the compound carbaNAD known in the literature (J. T. Slama, Biochemistry (1988), 27, 183 and Biochemistry (1989), 28, 7688). Other stable coenzymes which can be used are described in International Patent Publication Nos. WO 98/33936, WO 01/49247, and WO 2007/012494, U.S. Pat. Nos. 5,801,006 and 7,553,615, and the publication Blackburn et al. (Chem. Comm. (1996), 2765), the disclosures of which are hereby incorporated herein by reference in their entirety.

The diagnostic test element described within the scope of the present application can be any test element which includes a dry reagent layer containing the enzyme and the stabilized coenzyme and can be wetted by the sample containing the analyte. In addition to the enzyme and the stabilized coenzyme, the reagent layer can optionally contain further reagents which facilitate the qualitative detection or the quantitative determination of the analyte such as, for example, mediators, optical indicators as well as suitable auxiliary substances and/or additives.

The term "mediator" as used within the scope of this application means a chemical compound which oxidizes the reduced coenzyme obtained by reaction with the analyte and thus increases the reactivity of the coenzyme. Mediators which can be used according to the present application include, among others, nitrosoanilines such as for example [(4-nitrosophenyl)imino]dimethanol hydrochloride, quinones such as for example phenanthrene quinone, a phenanthroline quinone or a benzo[h]-quinoline quinone, phenazines such as for example 1-(3-carboxypropoxy)-5-ethyl-phenazinium-trifluoromethane sulfonate and/or diaphorase (EC 1.6.99.2).

A quinone, and in particular but not exclusively a 1,10-phenanthroline quinone, a 1,7-phenanthroline quinone, a 4,7-phenanthroline quinone or N-alkylated or N,N'-dialkylated salts thereof may be used as the mediator. In this connection, N-methyl-1,10-phenanthrolinium-5,6-quinone, N,N'-dimethyl-1,10-phenanthrolinium-5,6-quinone, N-methyl-1,7-phenanthrolinium-5,6-quinone, N,N'-dimethyl-1,7-phenanthrolinium-5,6-quinone, N-methyl-4,7-phenanthrolinium-5,6-quinone and N,N'-dimethyl-4,7-phenanthrolinium-5,6-quinone have proven to be particularly advantageous where in the case of N-alkylated or N,N'-dialkylated salts any anion can act as the counterion of the mediator. In one particular embodiment, a halogenide or trifluoromethane sulfonate is used as the counterion.

Any substance that is reducible and undergoes a detectable change in its optical properties such as, for example, colour, fluorescence, remission, transmission, polarization and/or refractive index can be used as the optical indicator. The determination of the presence and/or the amount of analyte in the sample can take place using the naked eye and/or by means of a detection device using an optical method, for example by photometric or fluorimetric determination, or an electrochemical method that appears suitable to a person skilled in the art. Heteropoly acids, and in particular 2,18-phosphomolybdic acid, may be used as optical indicators that are reduced to the corresponding heteropoly blue.

In one embodiment, the diagnostic test element in addition to the storage container is also essentially free of desiccants. With respect to diagnostic test elements, the term "essentially free of desiccants" means that the diagnostic test element contains an amount of <5% by weight, <1% by weight, <0.1% by weight, <0.01% by weight or <0.001% by weight desiccant based on the total weight of the test chemistry of the diagnostic test element. The possibility of reducing the amount of desiccant or of completely dispensing with desiccants within the scope of producing and storing the test elements described herein has the advantage that the production as well as storage of the test elements can be simplified and thus carried out more cost-effectively.

In a further embodiment, a diagnostic test element additionally includes a needle element for making a small incision in the skin which can consist of any material, including but not limited to a metal or plastic, and may be integrated into the diagnostic test element, in addition to the enzyme and the stabilized coenzyme. An integrated needle element in the sense of the present application is understood as a needle element which is physically joined to the diagnostic test element. In contrast, a separate needle element is defined as a needle element that is present separate from the diagnostic test element and has no physical connection to the diagnostic test element.

The needle element may be used to make a small incision in the skin to release body fluids such as, for example, blood which can be examined for an analyte using the diagnostic test element described herein. In this case, the released body fluid can be transferred directly or indirectly onto the diagnostic test element for example by using a sampling element. In this connection, any element which is capable of taking up a sufficient amount of body fluid to determine the analyte and enables the subsequent transfer of at least some of the body fluid that has been taken up onto the diagnostic test element can be used as the sampling element. In one aspect, the use of capillaries is suitable for enabling subsequent transfer of at least some of the body fluid that has been taken up onto the diagnostic test element. Similarly, in one form the needle element used to make a small incision in the skin additionally includes a capillary channel by means of which released body fluid can be taken up and transferred onto the diagnostic test element utilizing capillary forces.

In one aspect, the storage containers disclosed herein enable the diagnostic test elements described above to be stored for a relatively long period if necessary at a relative air humidity of at least 50% and/or at a temperature of at least 20° C. without significant loss of enzyme activity. This means that the diagnostic test element has a reduction of enzyme activity of less than 50%, less than 30%, or less than 20% based on the initial value of enzyme activity for example after storage for a period of at least 4 weeks, at least 8 weeks or at least 12 weeks at a temperature of at least 20° C., at least 25° C. or at least 30° C.

Methods and tests for determining the activity of enzymes are well-known in the prior art and, if required, can be adapted by a person skilled in the art to the respective requirements, where the same test conditions are used in each case to compare the enzyme activity before and after storage.

The diagnostic test elements stored by means of the storage containers disclosed herein can be used to determine any biological or chemical substance which can be detected photochemically or electrochemically. The analyte may be selected from the group of malic acid, alcohol, ammonium, ascorbic acid, cholesterol, cysteine, glucose, glutathione, glycerol, urea, 3-hydroxybutyrate, lactic acid, 5'-nucleotidase, peptides, pyruvate, salicylate and triglycerides. In one particular form, the analyte is glucose. In this connection, the analyte can be derived from any source, but in particular and non-limiting forms is in a body fluid including but not limited to whole blood, plasma, serum, lymph fluid, bile, cerebrospinal fluid, extracellular tissue fluid, urine as well as glandular secretions such as, for example, saliva or sweat. The presence and/or the amount of an analyte in a sample of whole blood, plasma, serum or extracellular tissue fluid may be determined by means of the diagnostic test elements described herein.

The qualitative and/or quantitative determination of the analyte can take place in any manner. For this purpose, all methods for detecting enzymatic reactions previously known can generally be used which generate a measurable signal that can be evaluated or read-out manually or using suitable means. Non-limiting examples of suitable optical detection methods include, for example, the measurement of absorbance, fluorescence, circular dichroism (CD), optical rotation dispersion (ORD), refractometry etc. Electrochemical techniques may also be used. In one form, the analyte is detected photometrically or fluorometrically for example indirectly by means of a fluorometrically detectable change of the coenzyme.

A further aspect of the present application concerns a diagnostic product which includes a plurality of interconnected, individually separable test strips in a bar-like and/or roll-like arrangement, where the test strips each include an enzyme and a stabilized coenzyme. In one form, the diagnostic product includes of a plurality of interconnected, individually separable test strips in a bar-shaped and/or roll-shaped arrangement, where the test strips are defined as above. With regard to particular embodiments of the test strip, reference is made to the remarks regarding the diagnostic test elements described in the present application which are stored in the storage containers disclosed herein. In the case of a bar-shaped and/or roll-shaped arrangement of the test strips, it is possible to dispense with the presence of desiccants and/or sealing elements.

In a further aspect, an analytical measuring device includes a storage container described herein or a diagnostic product described herein and is used for the qualitative and/or quantitative determination of an analyte. Non-limiting examples of such analytical measuring devices include, among others, the commercially available products Accu-Chek® Active, Accu-Chek® Compact and Accu-Check® Mobile (all from the Roche Company).

EXAMPLES

The following examples are for illustration purposes and are not to be construed as limiting the invention disclosed in this document to only the embodiments disclosed in these examples.

Example 1

CarbaNAD (FIG. 1) or NAD was added to the glucose-specific GlucDH. These formulations were each applied to Pokalon foil (Lonza) and after drying stored under warm and moist conditions (32° C., 85% relative air humidity). Subsequently, the reaction kinetics and the function curve were determined at regular intervals. cNAD/NAD analyses and a determination of the residual activity of the enzyme were carried out concurrently to the respective measurement dates.

Figure 2A:
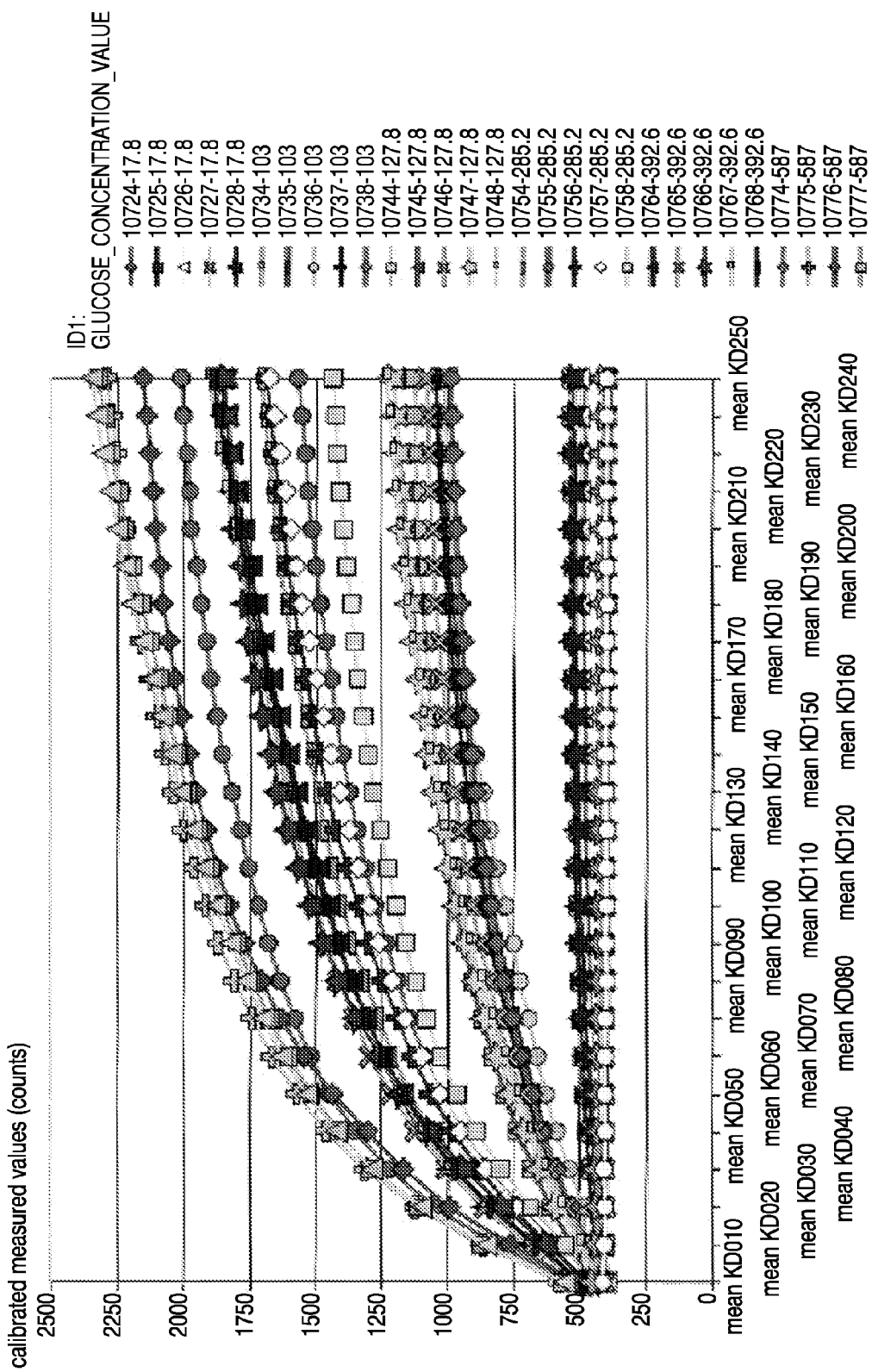
FIG. 2A is a graphical illustration of the enzyme kinetics of glucose dehydrogenase in the presence of NAD after 1 day.
Figure 2B:
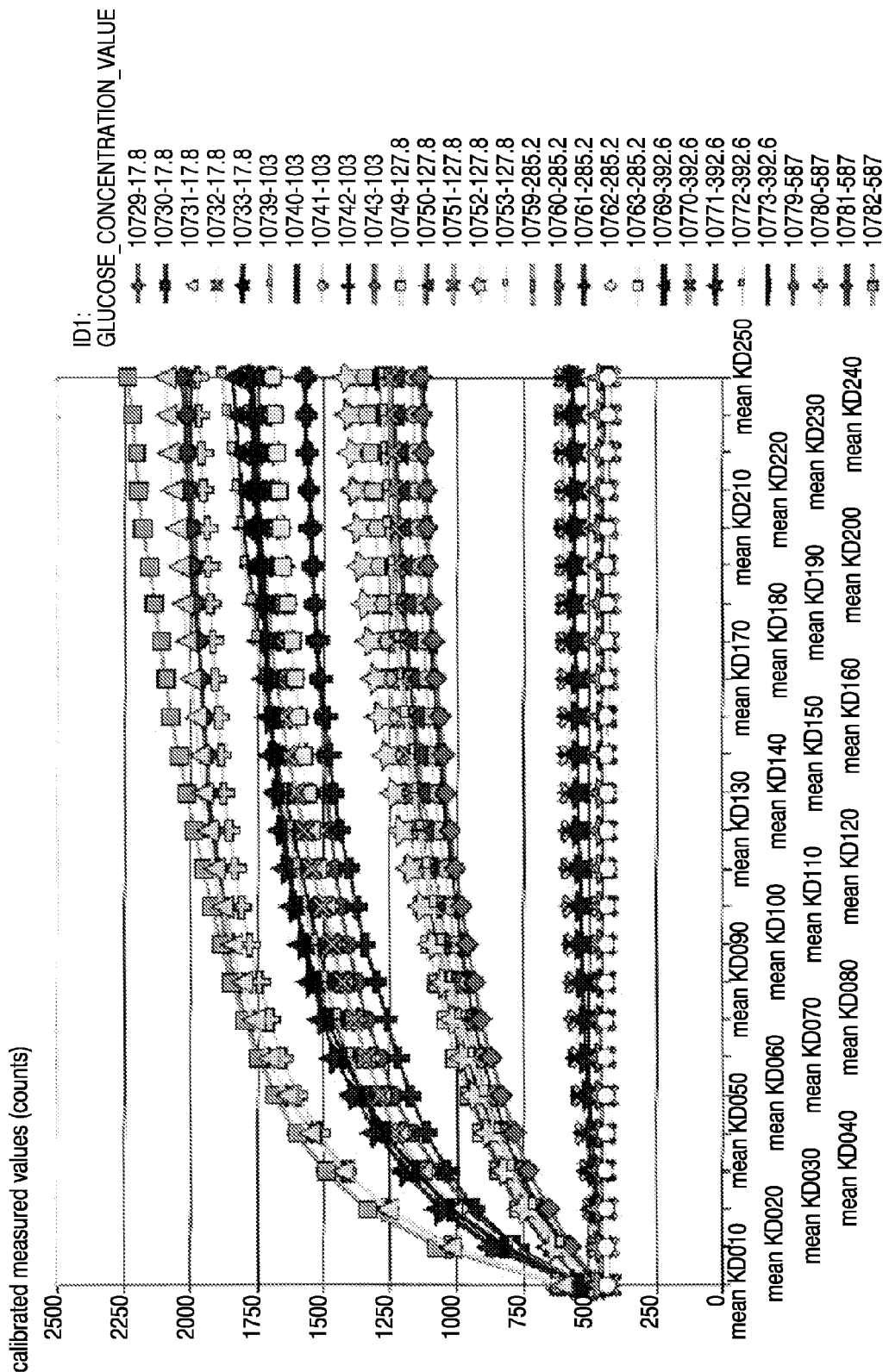
FIG. 2B is a graphical illustration of the enzyme kinetics of glucose dehydrogenase in the presence of cNAD after 1 day.
Figure 2C:
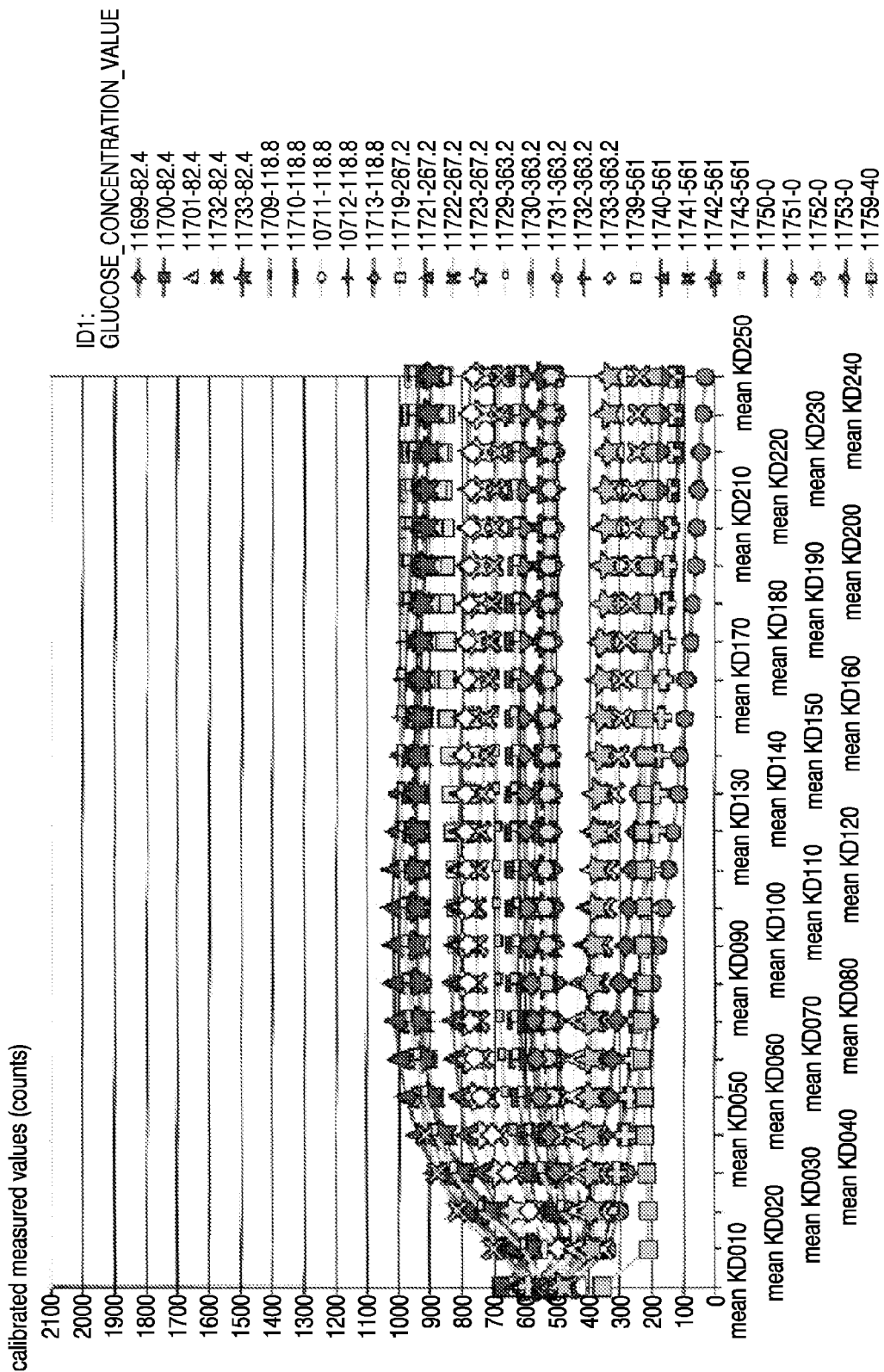
FIG. 2C is a graphical illustration of the enzyme kinetics of glucose dehydrogenase in the presence of NAD after 5 weeks storage at 32° C. and 85% relative air humidity.
Figure 2D:
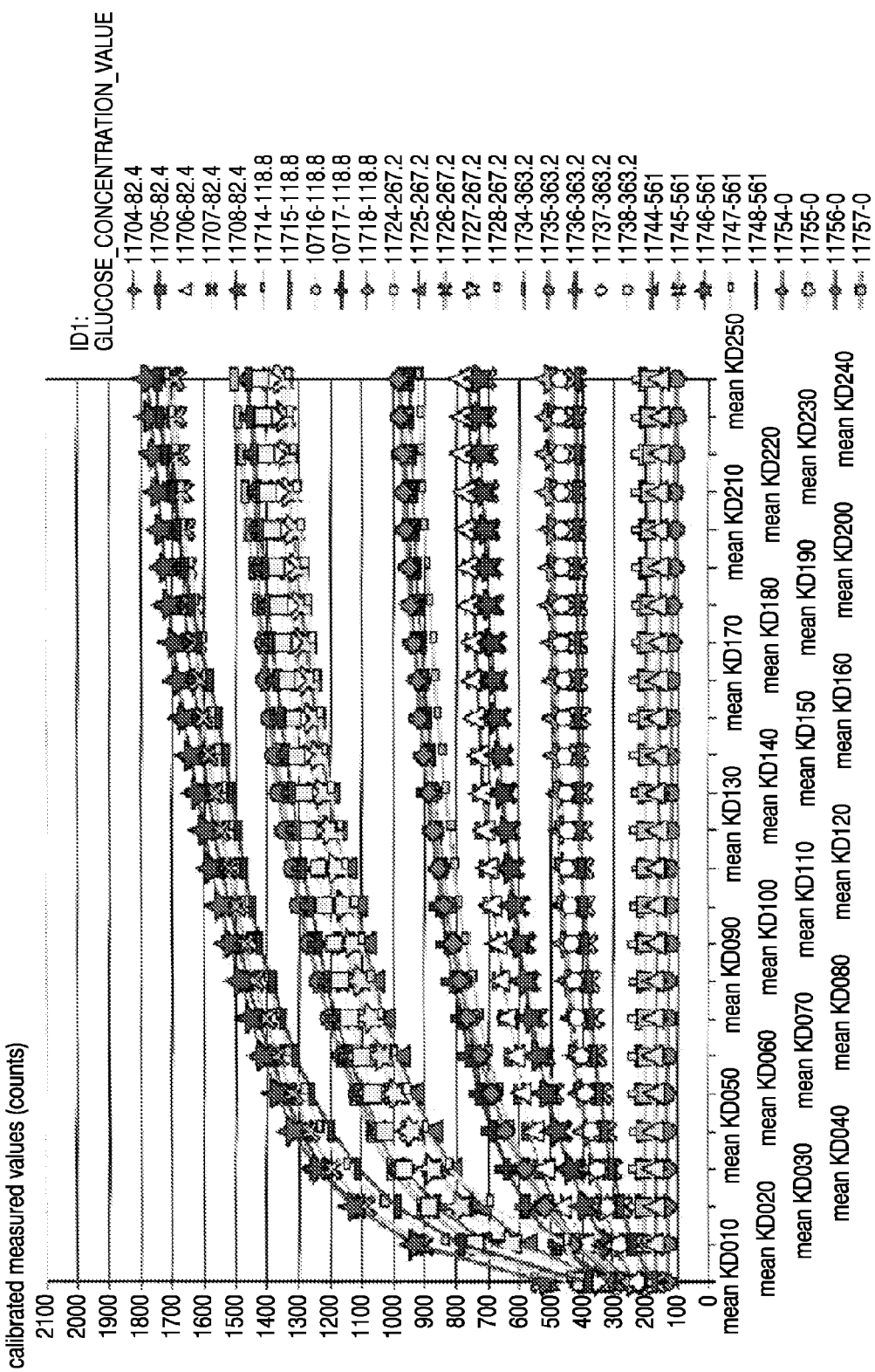
FIG. 2D is a graphical illustration of the enzyme kinetics of glucose dehydrogenase in the presence of cNAD after 5 weeks storage at 32° C. and 85% relative air humidity.

The kinetic curves for NAD (FIG. 2A) and cNAD (FIG. 2B) determined on the first day are comparable and also exhibit a similar amplitude in their glucose dependency. However, after 5 weeks a clear difference in the kinetic curves can be seen. Whereas the kinetics for NAD (FIG. 2C) decreases strongly in its dynamics, the kinetics of the enzyme stabilized with cNAD remains almost unchanged (FIG. 2D).

Figure 3:
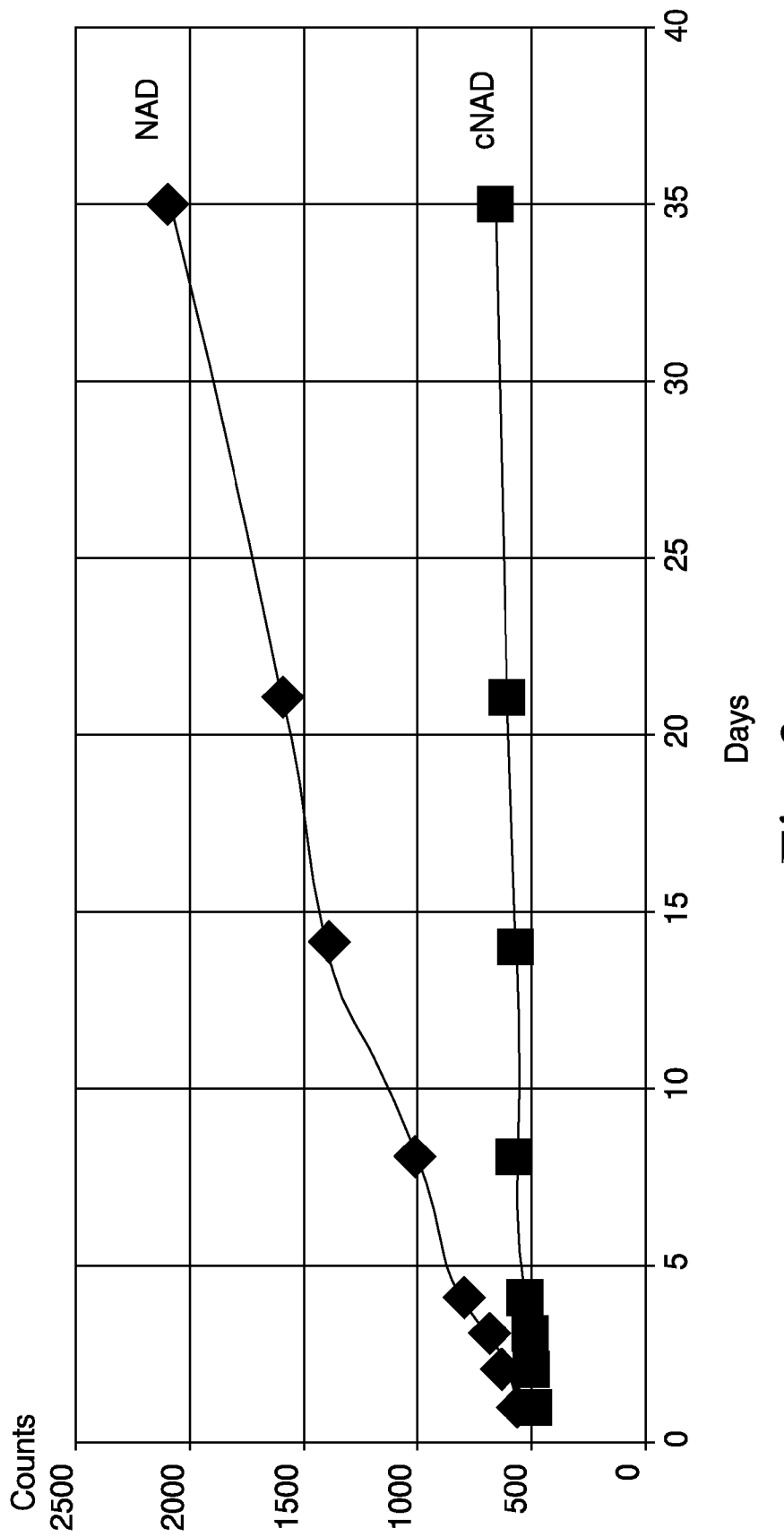
FIG. 3 illustrates a graphical comparison of the blank values of glucose dehydrogenase in the presence of NAD or of GlucDH in the presence of cNAD for a period of up to 5 weeks at 32° C. and 85% air humidity.

There is also a distinct difference in the blank values (dry blank value before application of a blood sample) as shown in FIG. 3. The increase of the dry blank value for NAD is attributable to the formation of fluorescent particles (N. J. Oppenheimer, in the Pyridine Nucleotide Coenzymes, Academic Press New York, London 1982, editor J. Everese, B. Anderson, K. You, Chapter 3, pages 56-65). Surprisingly, this does not occur with cNAD.

Figure 4:
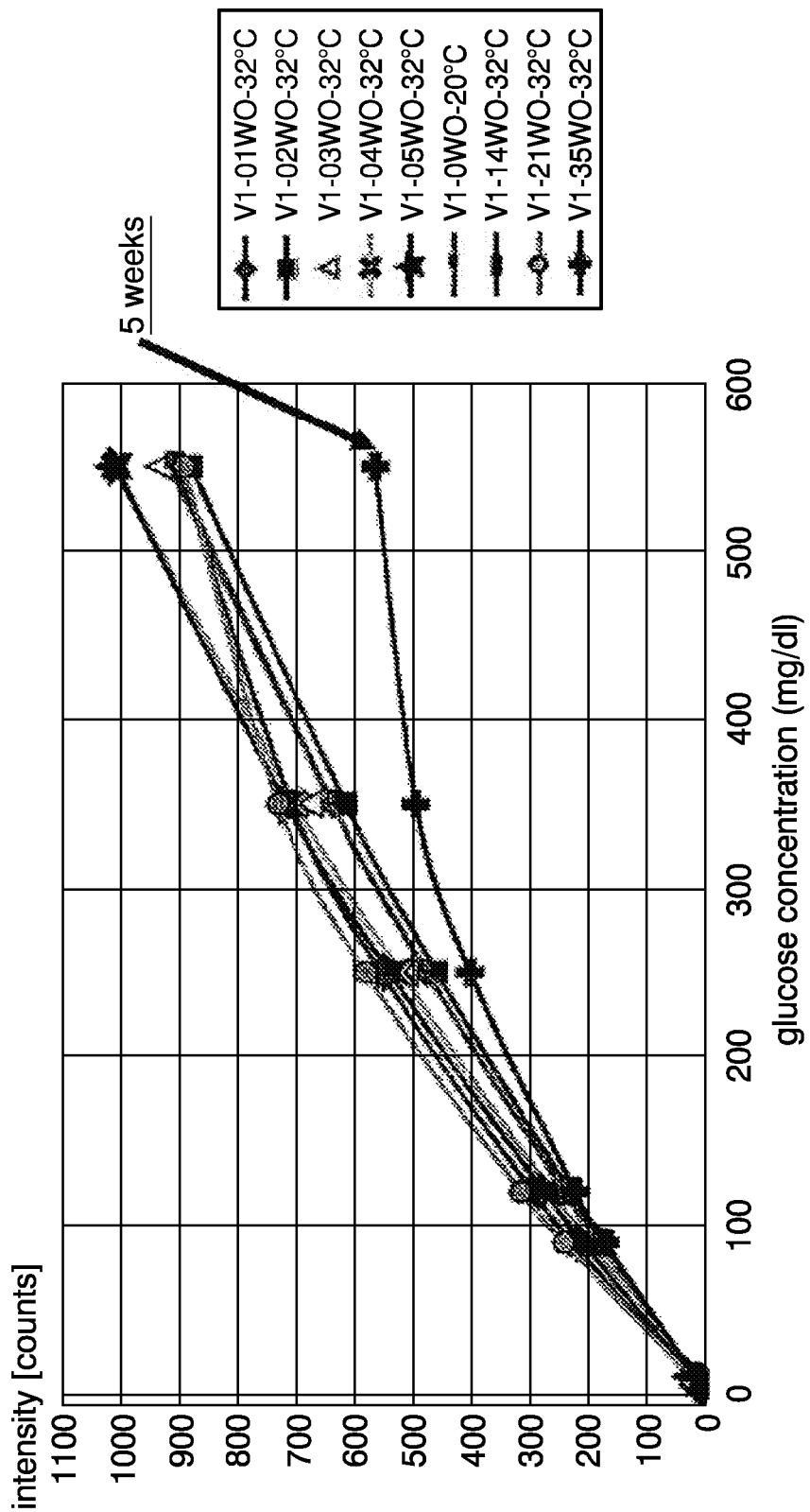
FIG. 4 is a graphical illustration of various function curves of glucose dehydrogenase after storage of glucose dehydrogenase in the presence of NAD at 32° C. and 85% air humidity for periods between 1 day and 5 weeks.
Figure 5A:
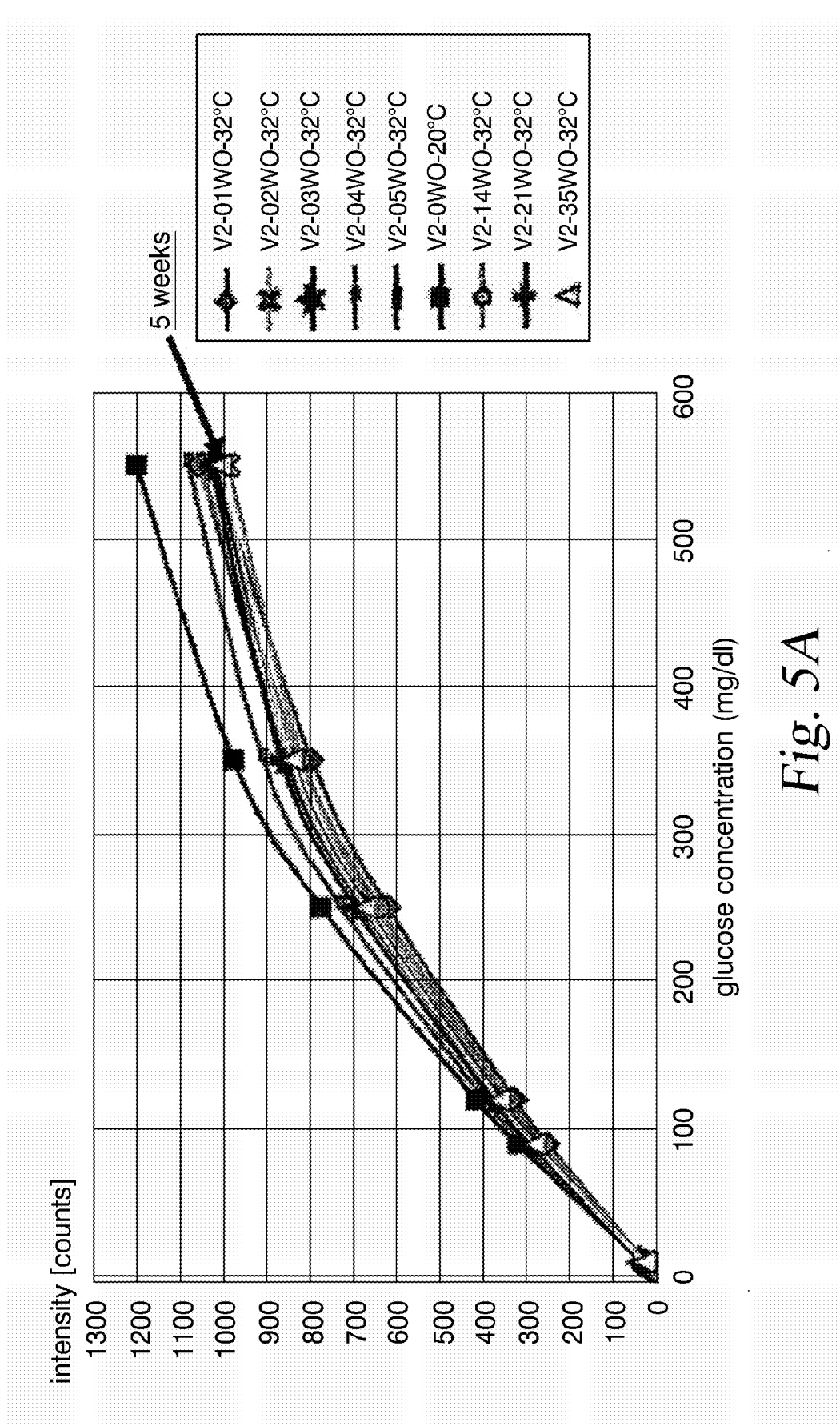
FIGS. 5A and 5B are graphical illustrations of various function curves of glucose dehydrogenase after storage of glucose dehydrogenase in the presence of cNAD at 32° C. and 85% air humidity for periods between 1 day and 5 weeks (FIG. 5A) or between 1 day and 24 weeks (FIG. 5B).
Figure 5B:
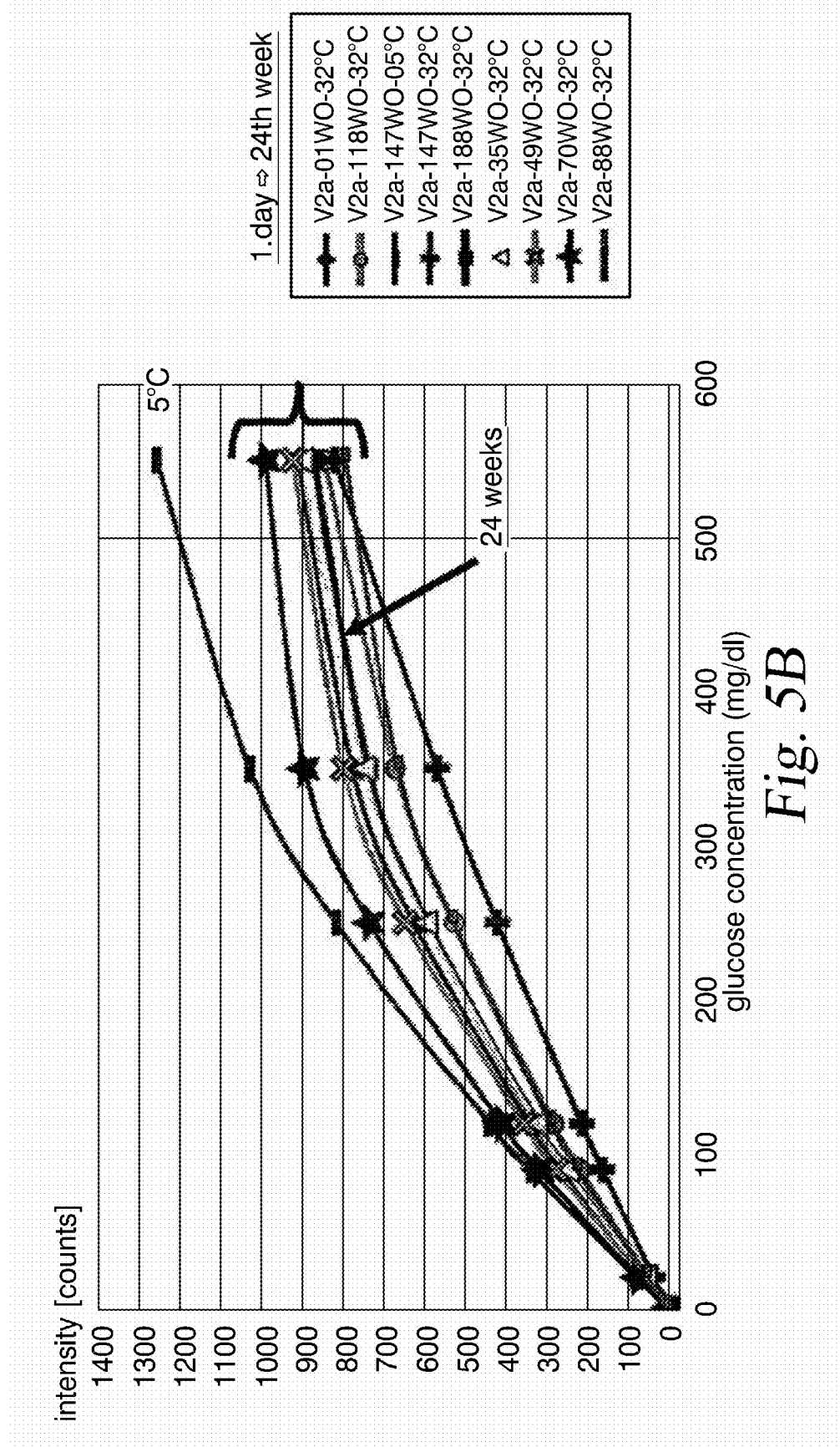

The different stability of glucose dehydrogenase in the presence of NAD and cNAD is also evident from a comparison of FIGS. 4 and 5. After 5 weeks the function curve for the enzyme stabilized with cNAD is still in the bunch of previous measurements (FIG. 5A), whereas the curve for the enzyme treated with NAD (FIG. 4) shows a fall-off at higher concentrations which is a typical sign for inadequate amounts of enzyme/coenzyme. FIG. 5B shows various function curves for glucose dehydrogenase stabilized with cNAD over a period of 24 weeks. It is clear in this connection that the function of the enzyme is only slightly changed at high glucose concentrations throughout the entire period and approximately corresponds after 24 weeks to the value obtained after 5 weeks.

Figure 6:
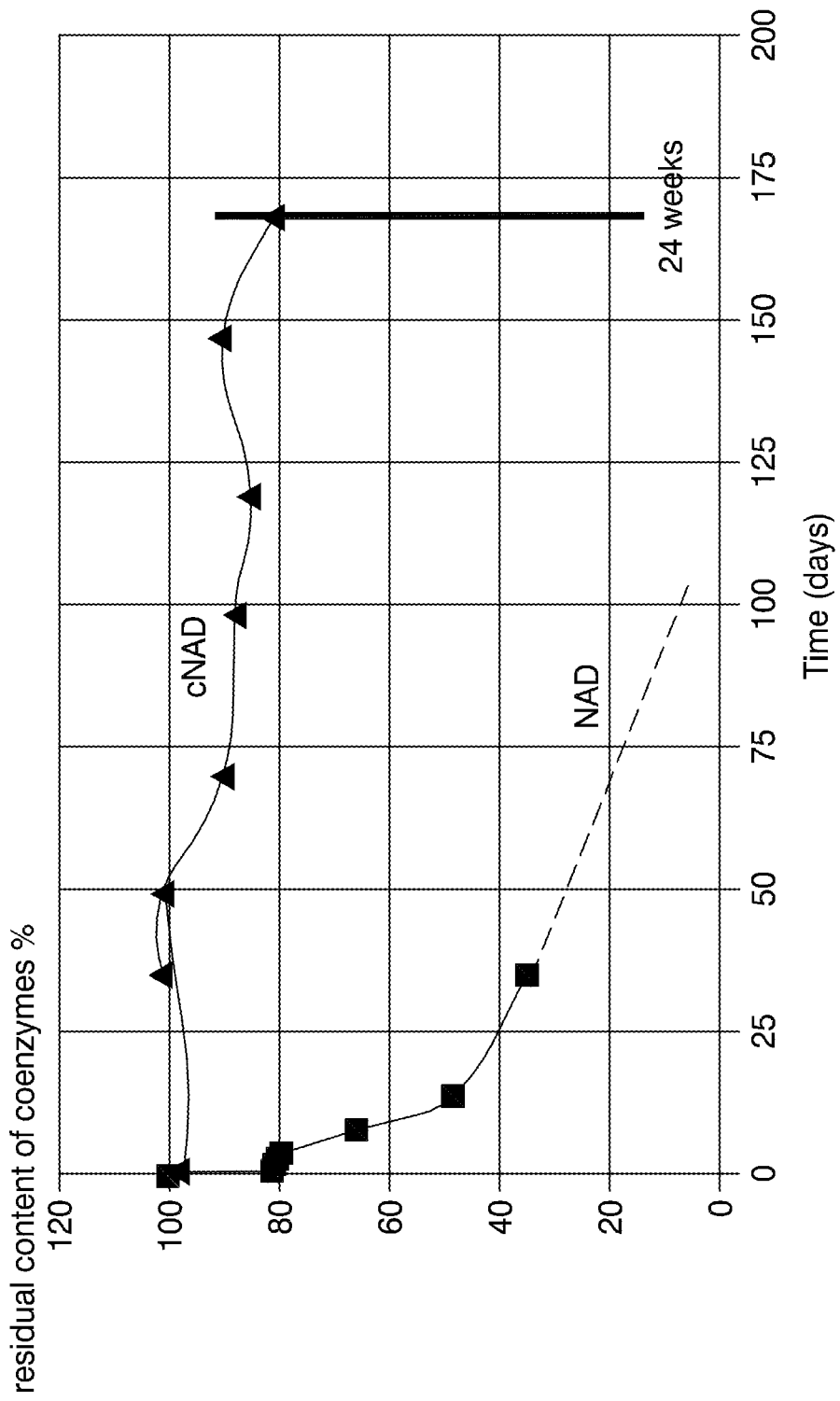
FIG. 6 is a graphical illustration of the residual content of NAD and cNAD after storage of glucose dehydrogenase in the presence of NAD or cNAD for 24 weeks at 32° C. and 85% air humidity.

The relation between the structure of the coenzyme and its stability over a predetermined period is evident from FIG. 6. According to this the residual content of cNAD in a glucose detection reagent after storage (at 32° C. and 85% relative air humidity) for 24 weeks is still about 80% of the initial value, whereas the content of NAD in a glucose detection reagent stabilized with NAD already declines after 5 weeks to about 35% of the initial value and, by extrapolation, is reduced to zero after about 17 weeks.

Figure 7A:
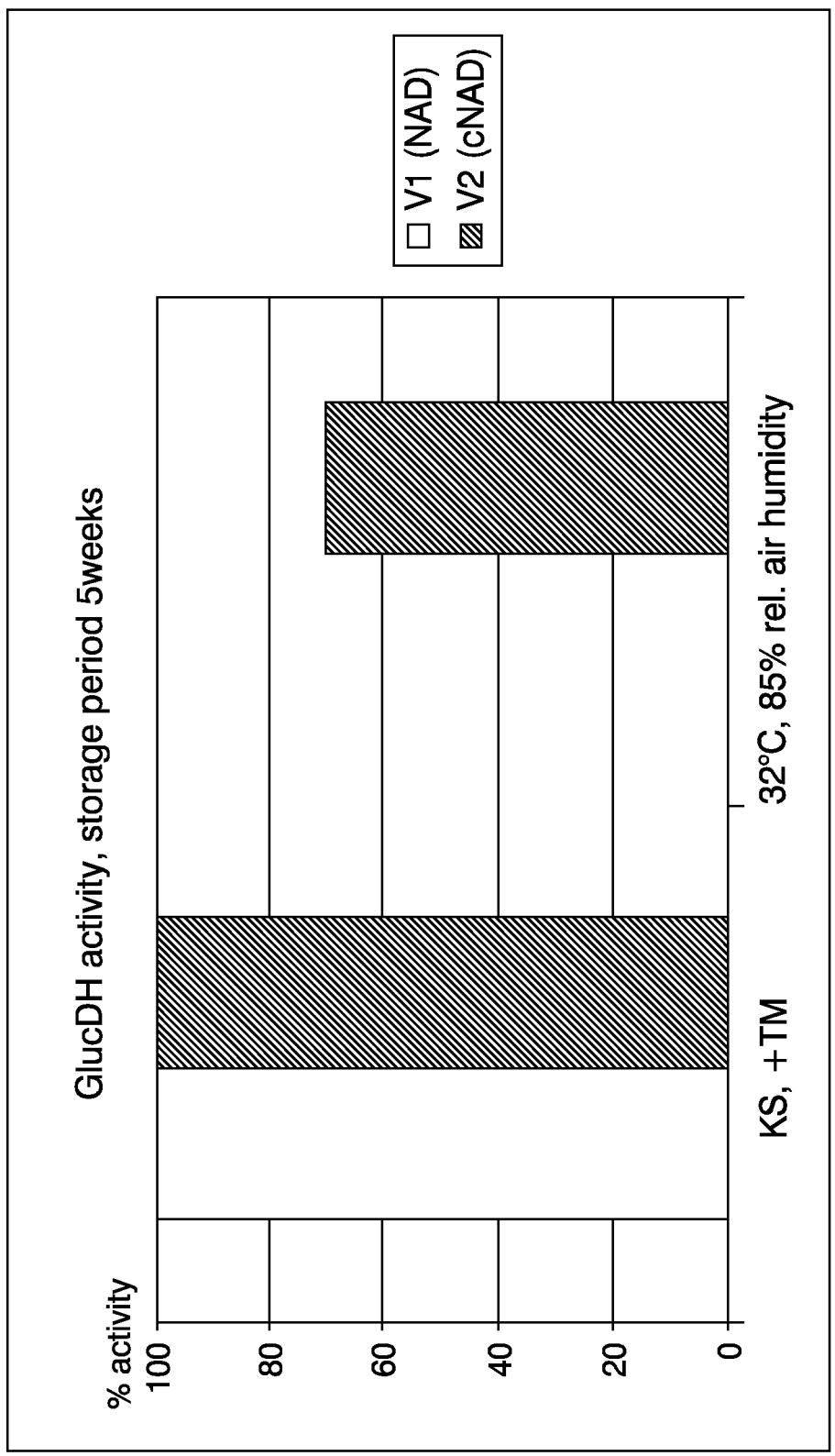
FIGS. 7A and 7B are graphical illustrations of the GlucDH activity after storage of glucose dehydrogenase in the presence of NAD or cNAD for 5 weeks (FIG. 7A) or 24 weeks (FIG. 7B) at 32° C. and 85% air humidity.
Figure 7B:
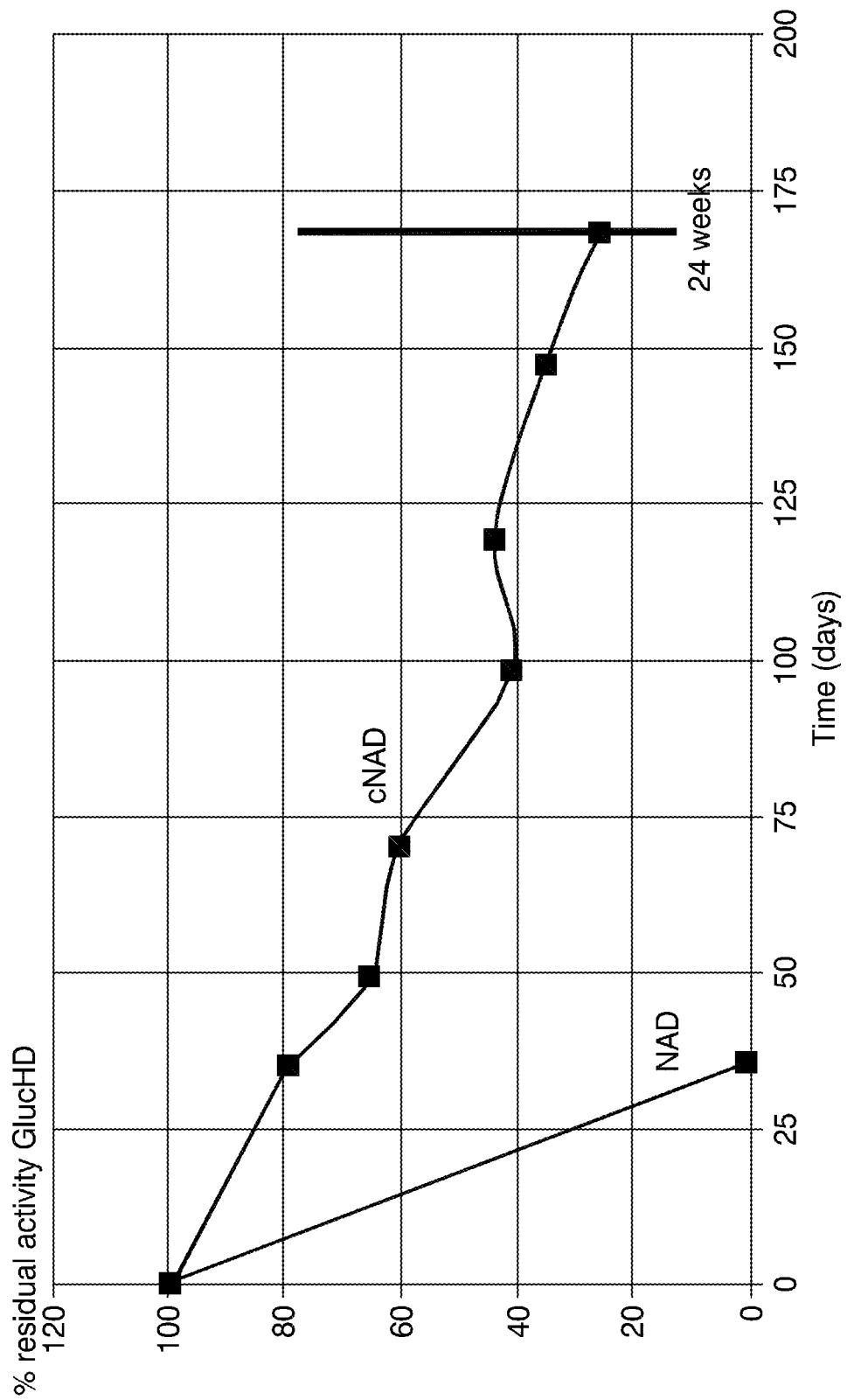

The result of the determination of the residual activity of the active GlucDH enzyme after 5 weeks at 32° C. and 85% relative air humidity (FIG. 7A) is completely surprising. The enzyme stabilized with NAD now only has an extremely low enzyme activity (0.5%), whereas the enzyme stabilized with cNAD still has a residual activity of 70% (in each case by comparison with samples stored in a refrigerator (KS) with desiccant (TM)). After 24 weeks at 32° C. and 85% relative air humidity (FIG. 7B), the residual activity of the enzyme when stabilized with cNAD is still about 25%.

Figure 8A:
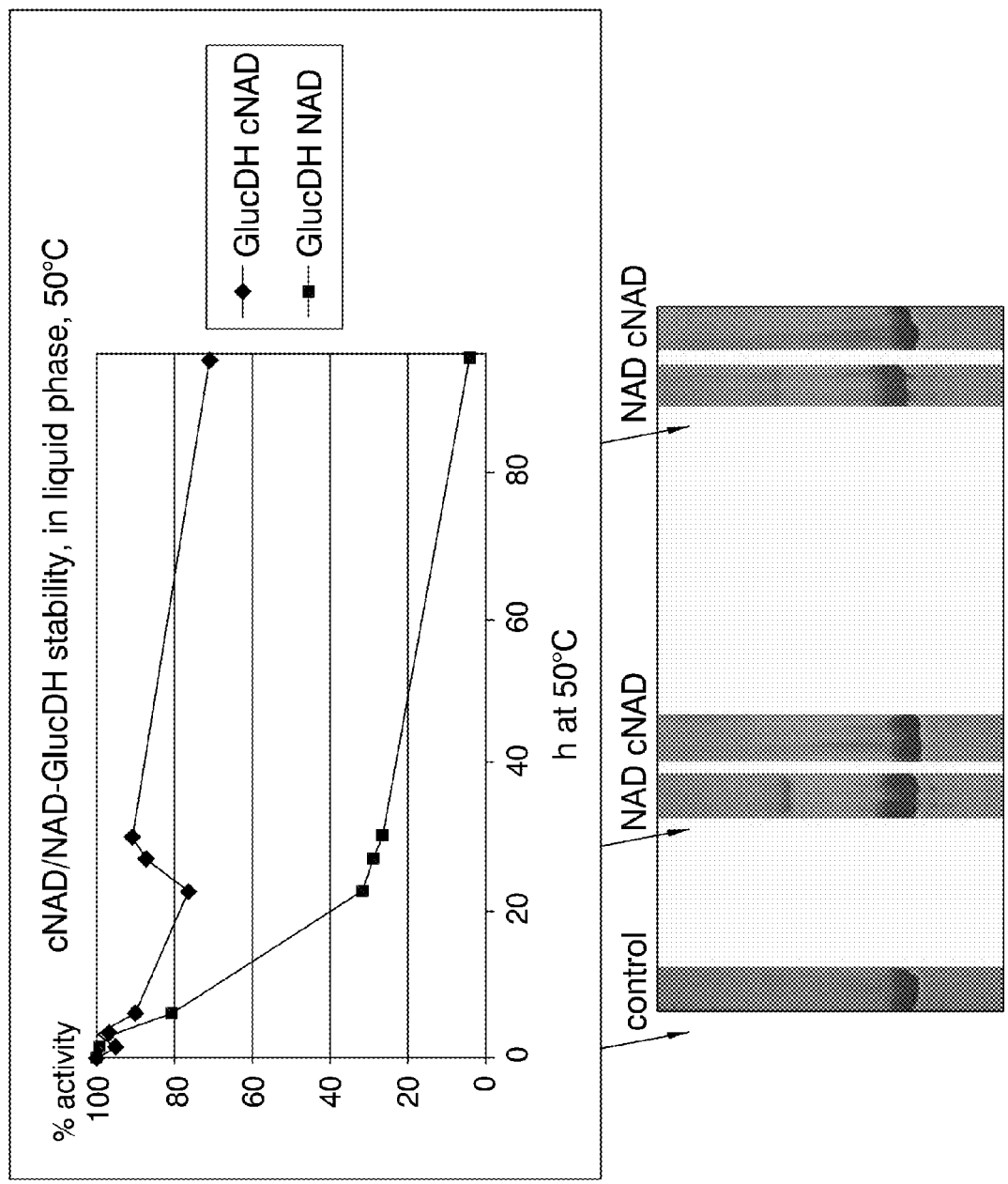
FIGS. 8A and 8B are graphical illustrations of the stability of glucose dehydrogenase in the presence of NAD or cNAD in the liquid phase at 50° C. over a period of 4 days (FIG. 8A) or 14 days (FIG. 8B) with test conditions of: GlucDH 10 mg/ml; NAD or cNAD 12 mg/ml, buffer: 0.1 M Tris, 1.2 M NaCl, pH 8.5; temperature 50° C.
Figure 8B:
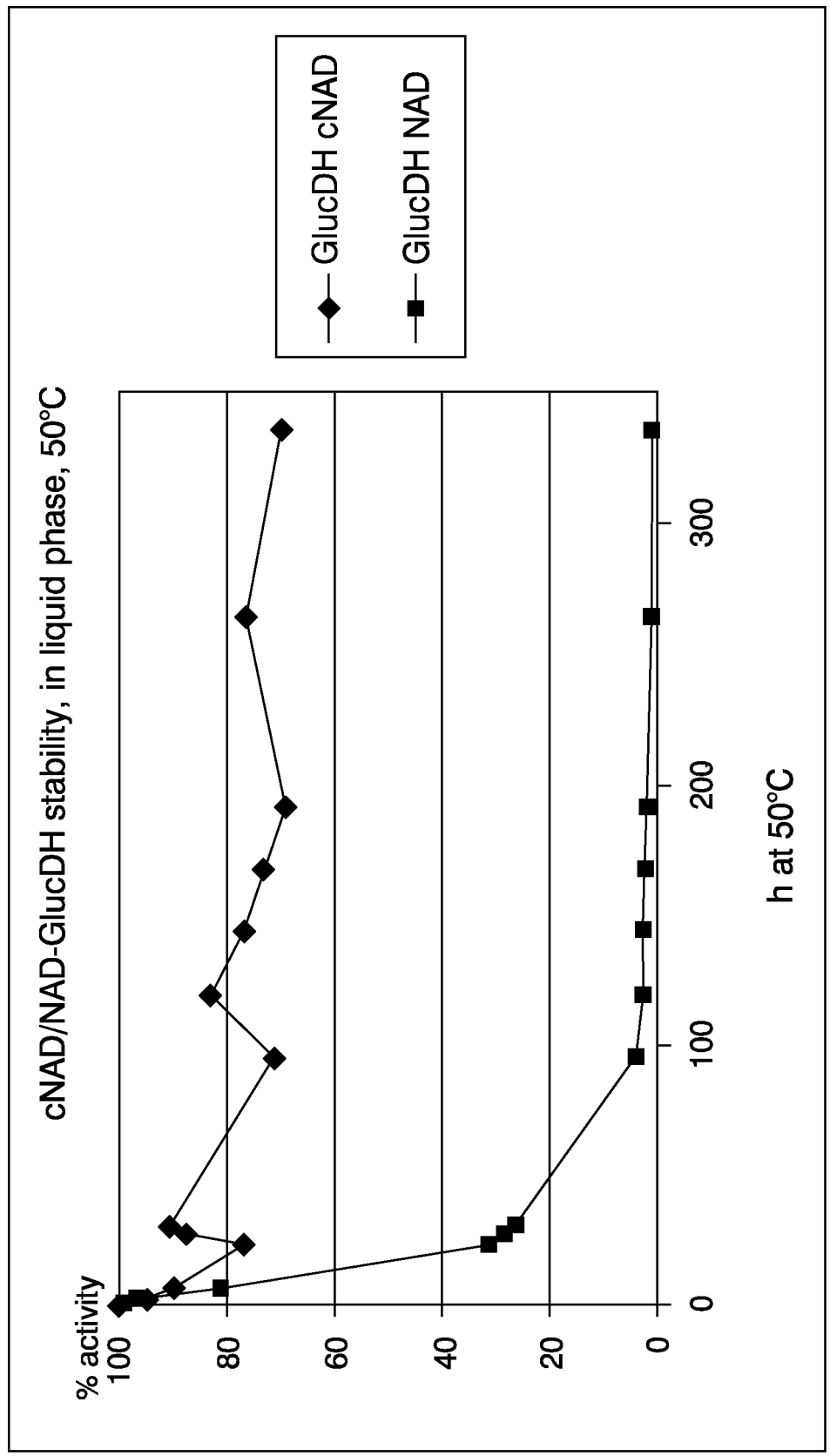

Storage of glucose dehydrogenase in a liquid phase also clearly shows the difference between NAD and cNAD (FIGS. 8A and 8B). The residual activity of glucose dehydrogenase in the presence of the native coenzyme NAD is >>5% after 95 hours at 50° C. whereas the residual activity of the GlucDH in the presence of the artificial coenzyme cNAD is 75% (FIG. 8A). After 336 hours storage at 50° C. the residual activity of the enzyme stabilized with NAD is now only about 1%; a residual activity of still about 70% was observed for the enzyme stored in the presence of cNAD. The corresponding SDS gels also show a change in the GlucDH bands in the presence of the native coenzyme NAD: new bands are seen at higher molecular masses and there is a shift of the 30 kDa band.

Overall it is an extremely surprising result that the stabilization of the cofactor simultaneously stabilizes the enzyme—and cannot just be due to the cooperative effect of the better cohesion of the enzyme. Decomposition of the cofactor NAD has a negative effect on the stability of the enzyme GlucDH and even accelerates its inactivation. Replacement of native NAD by artificial analogues allows GlucDH to be stored under stress conditions (e.g. elevated temperature) even in the presence of a cofactor.

It is possible with such a system to produce blood glucose test strips with considerably improved stability properties, in which a presentation without desiccant is possible.

Example 2 cNAD or NAD was added to a detection solution containing alcohol dehydrogenase. These mixtures were stored at 35° C. Subsequently, the stability of the enzyme was checked at regular intervals and the residual activity of the enzyme was determined.

Figure 9:
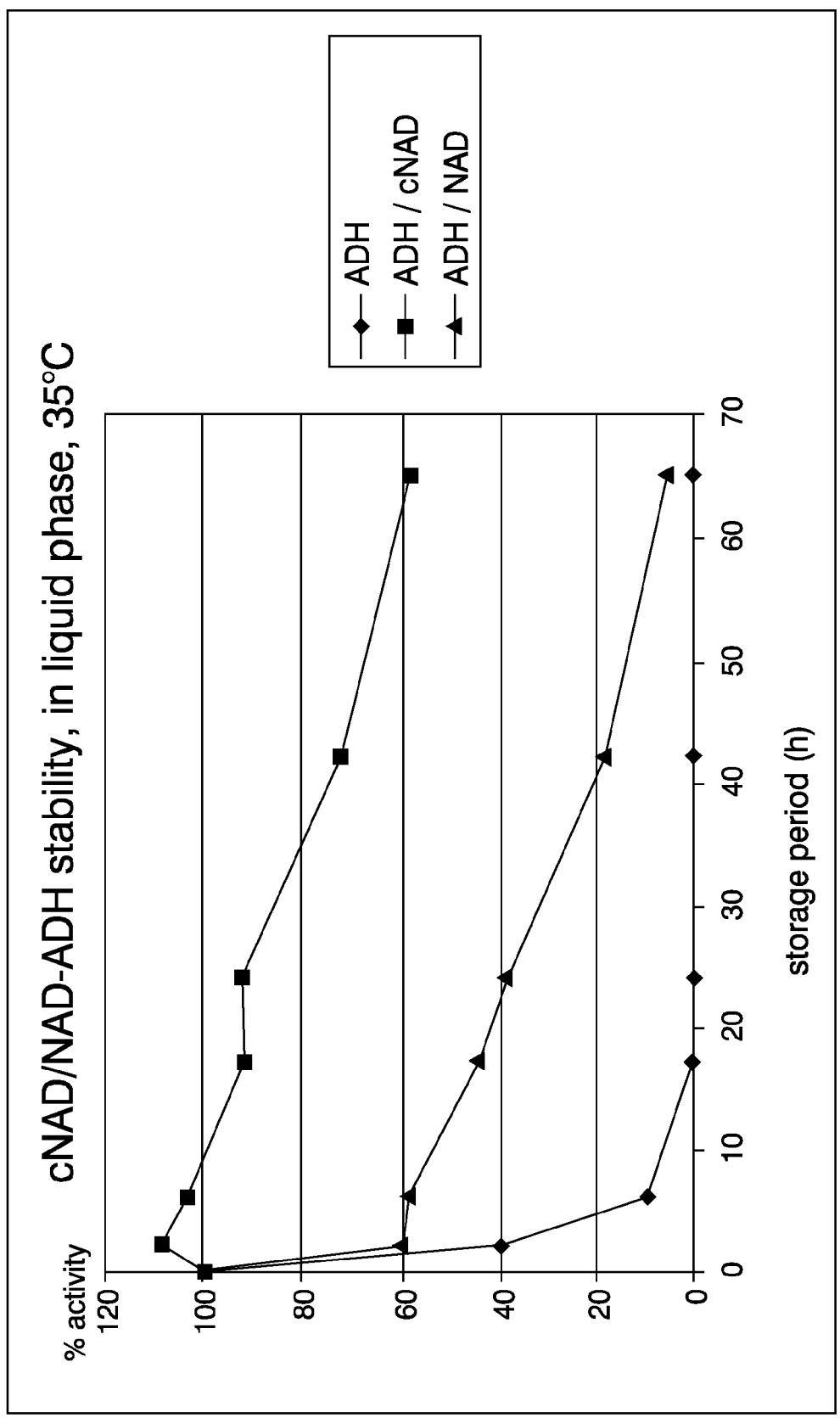
FIG. 9 is a graphical illustration of the stability of alcohol dehydrogenase from yeast in the presence of NAD or cNAD in the liquid phase at 35° C. over a period of 65 hours with test conditions of: ADH 5 mg/ml; NAD or cNAD 50 mg/ml; buffer: 75 mM $Na_4P_2O_7$, glycine, pH 9.0; temperature 35° C.

Once again storage in a liquid phase showed the difference between storage in the presence of NAD or cNAD (FIG. 9). After 65 hours at 35° C. the residual activity of alcohol dehydrogenase in the presence of the native coenzyme NAD was about 6%, whereas the residual activity of the enzyme in the presence of the artificial coenzyme cNAD is still about 60%.

Example 3

Figure 10A:
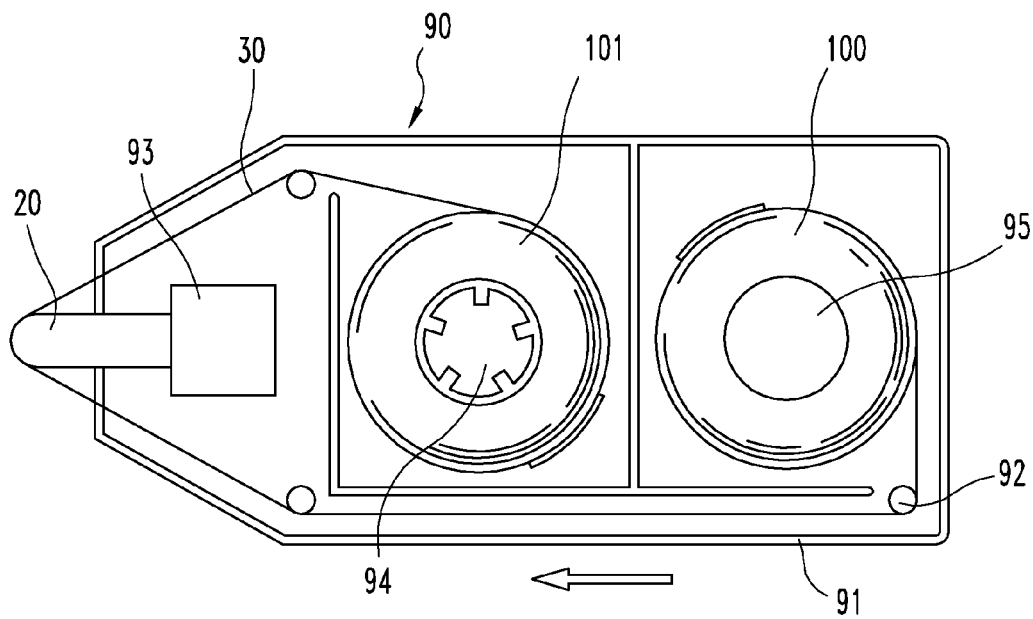
FIG. 10A is a plan view of a storage container in the form of a tape magazine having two chambers in which a test tape is used as the diagnostic test element.

FIG. 10A shows in cross-section an exemplary embodiment of a storage container in the form of tape magazine which can be inserted into an analytical measuring device. The storage container 90 has a housing 91 in which a supply spool 100 and a take-up spool 101 are positioned. The storage container additionally comprises a deflection tip 20 over the outer end of which a test tape 30 runs. The tape magazine has a first opening 93 at the inner end of the deflection tip to accommodate optical means.

In the embodiment shown, the tape magazine additionally has rollers or pins 92 to guide the test tape through the tape magazine as well as a second opening 94 for receiving a spool drive. The take-up spool with an axis of rotation 95 has an opening in its middle for this purpose as well as engaging elements for receiving the spool drive.

Figure 10B:
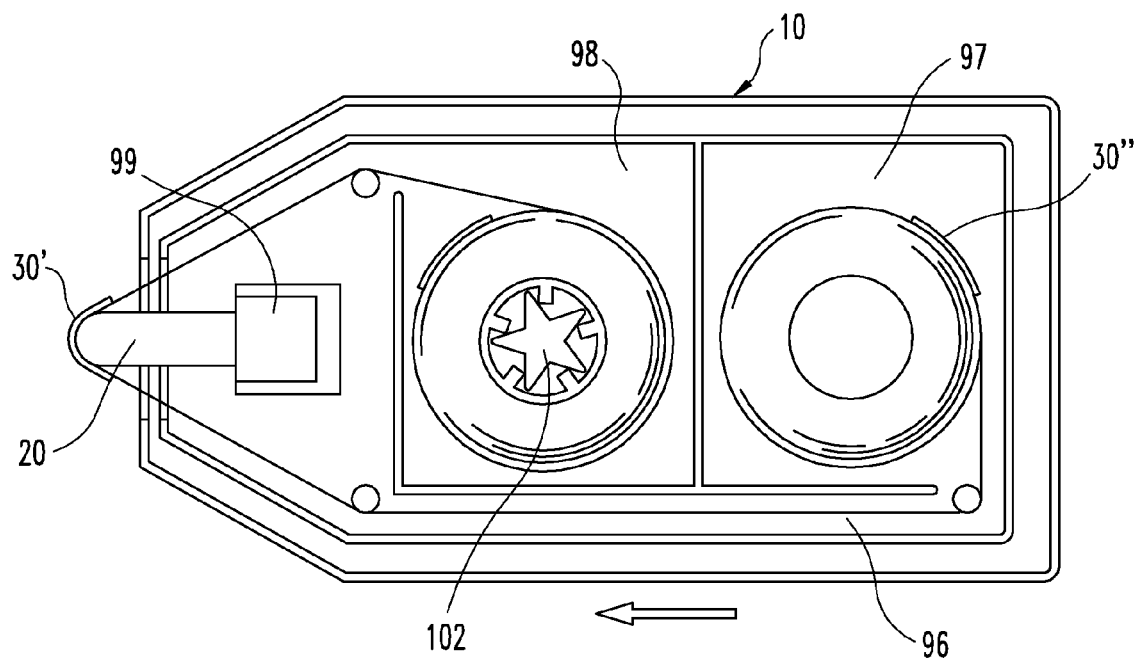
FIG. 10B is a plan view of an analytical measuring device containing the storage container illustrated in FIG. 10A.

FIG. 10B shows an analytical measuring device 10 in cross-section into which the tape magazine 90 described in connection with FIG. 10A is inserted. The analytical measuring device has a spool drive 102 which engages in the take-up spool 101 of the tape magazine and can for example be driven by a motor. In this connection, the spool drive enables a control and coordination of the transport of the test tape 30 into a sample application position or measuring position at the deflection tip 20 of the tape magazine where the measurement of the test tape wetted with a sample of the analyte can if necessary also be carried out at a different position such as, for example, in the interior of the tape magazine.

The analytical measuring device additionally comprises optical means 99 which are received in the first opening 93 as soon as the tape magazine is inserted into the analytical measuring device. If it is intended to carry out an optical measurement of the analyte, the optical system of the analytical measuring device must be coupled to the deflection tip 20 which, for example, can be achieved by using an optically transparent deflection tip or by introducing optical fibres into an otherwise light-impermeable deflection tip. The optical system of the analytical measuring device can for example envisage the use of optical fibres to which a light source and a detector are coupled.

FIG. 10B additionally shows a channel 96 within the tape magazine which is positioned between the deflection tip and the supply spool and in which the test tape is guided from the storage area 97 of the tape magazine to the deflection tip 20 before, after being brought into contact with a sample of the analyte at the deflection tip, it is returned into the take-up area 98 of the tape magazine. In this case the distance between individual test areas of the test tape can for example be selected such that a second test area 30" is still positioned within the tape magazine, whereas a first test area 30' is located in the sample application position or measuring position at the deflection tip 20, in order to, if necessary, ensure a protection against moisture or other external influences.

Example 4

Figure 11:
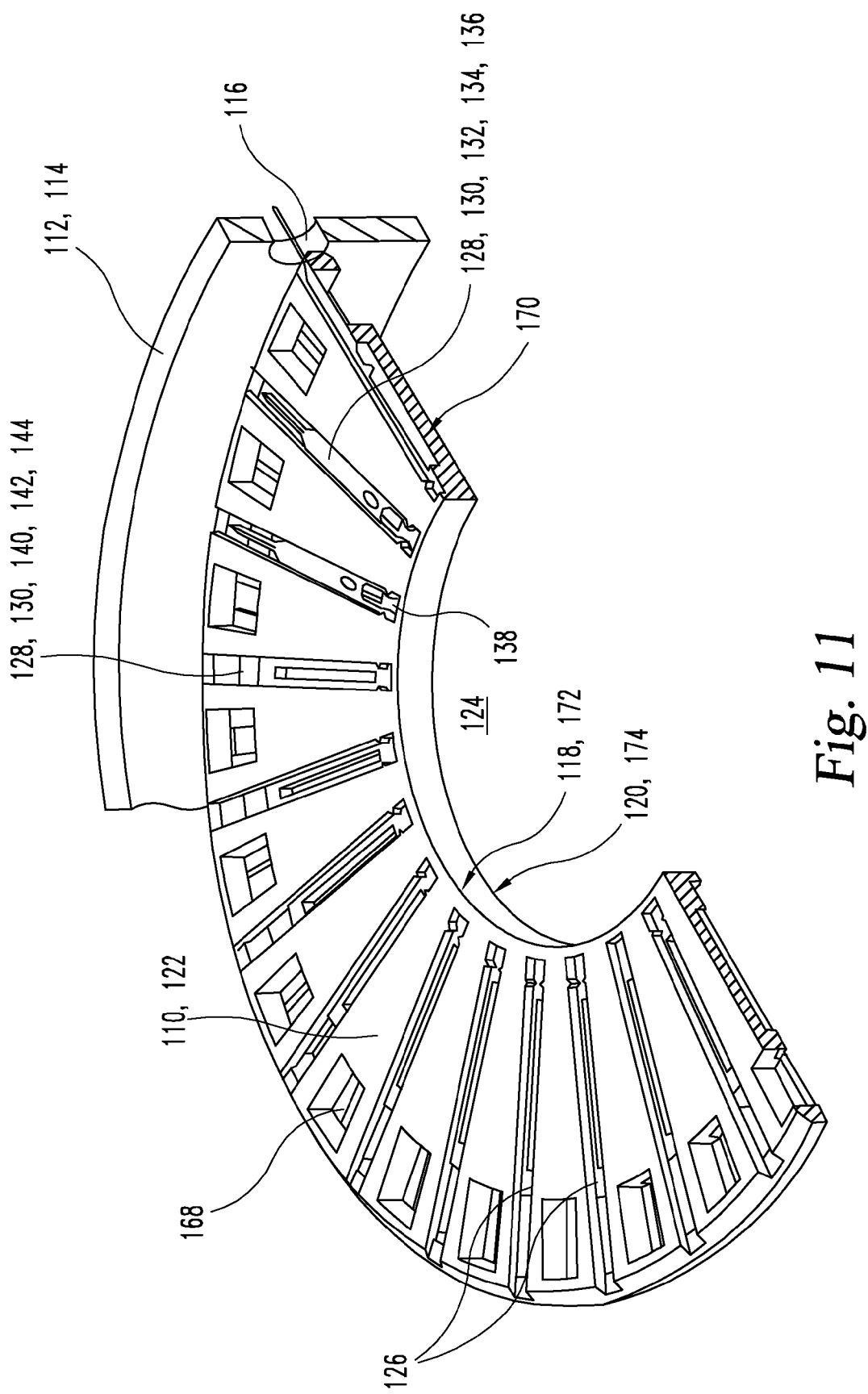
FIG. 11 is a perspective, partial section view of a storage container in the form of a disk-shaped turning magazine which accommodates a plurality of diagnostic test elements.
Figure 12:
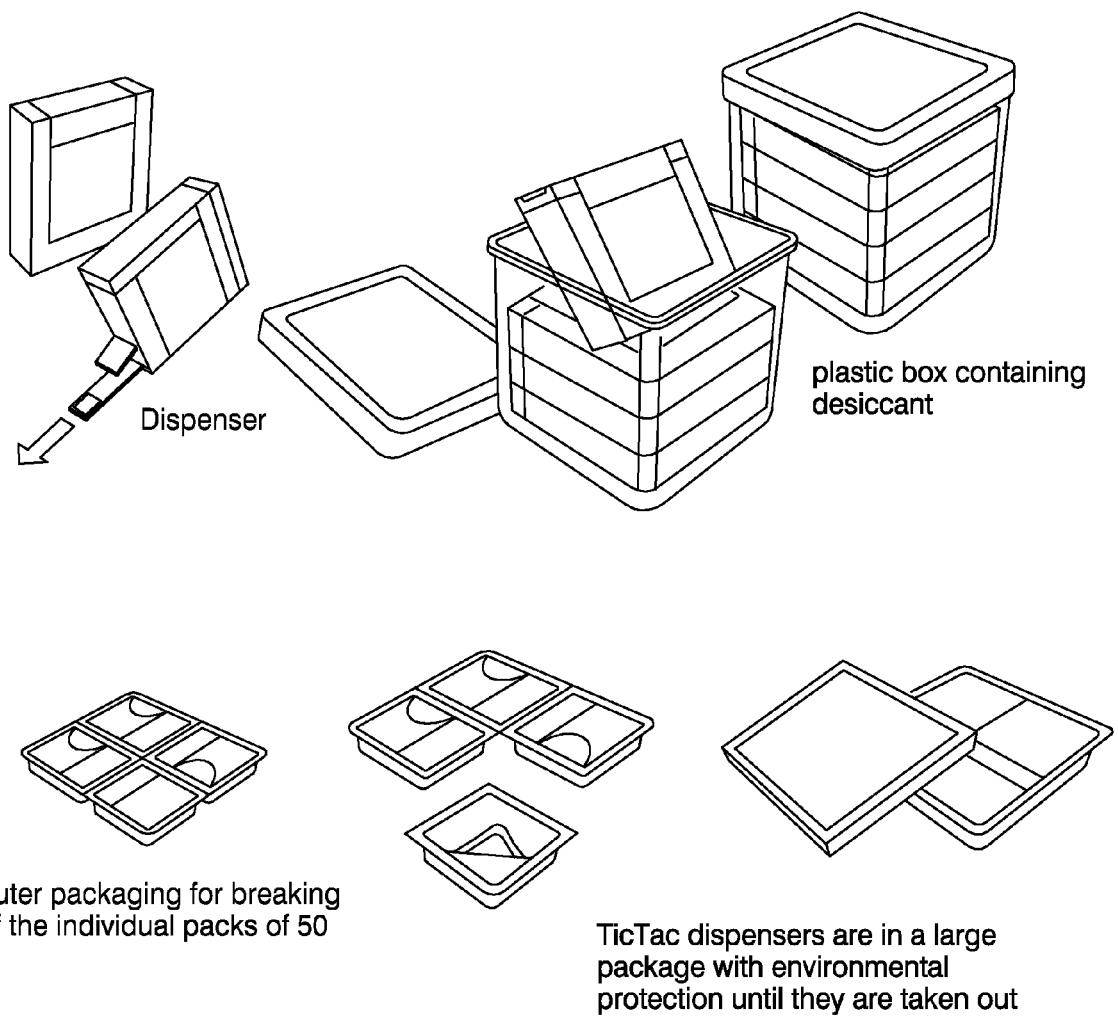
FIG. 12 is a schematic illustration of a storage container in the form of a TicTac® dispenser which contains a plurality of individual test strips as diagnostic test elements and is accommodated in an outer packaging filled with desiccant.
Figure 13:
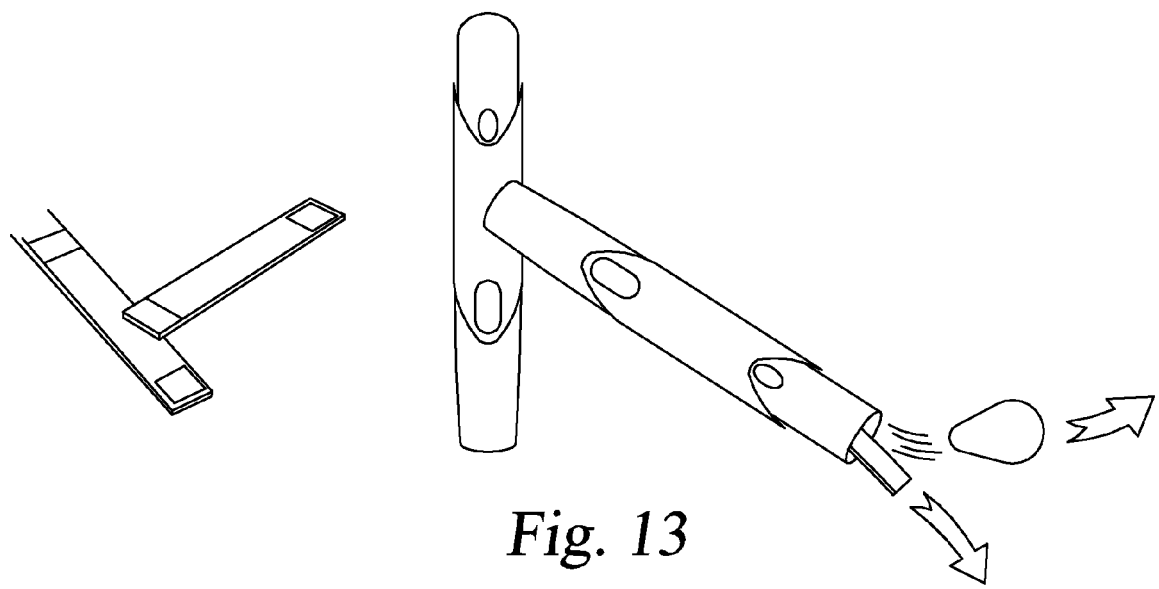
FIG. 13 is a perspective view of a storage container in the form of a lancing aid which contains an individual test strip as the diagnostic test element.
Figure 14A:
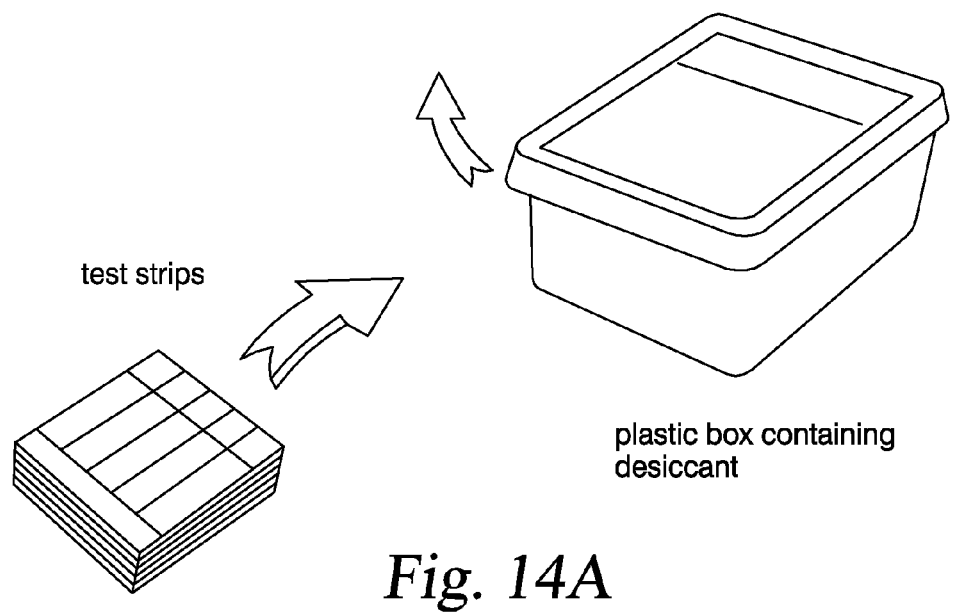
FIGS. 14A-C are perspective views of storage containers in the form of a plastic box containing desiccant (FIG. 14A), an aluminium can (FIG. 14B) and a plastic bag (FIG. 14C) which each contains a plurality of interconnected, individually separable test strips in a bar-shaped arrangement.
Figure 14B:
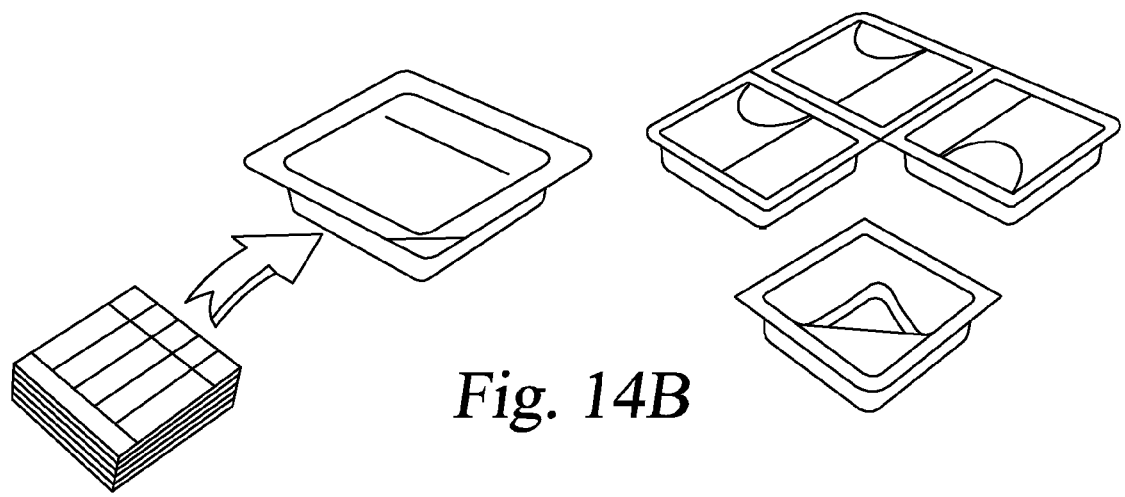
Figure 14C:
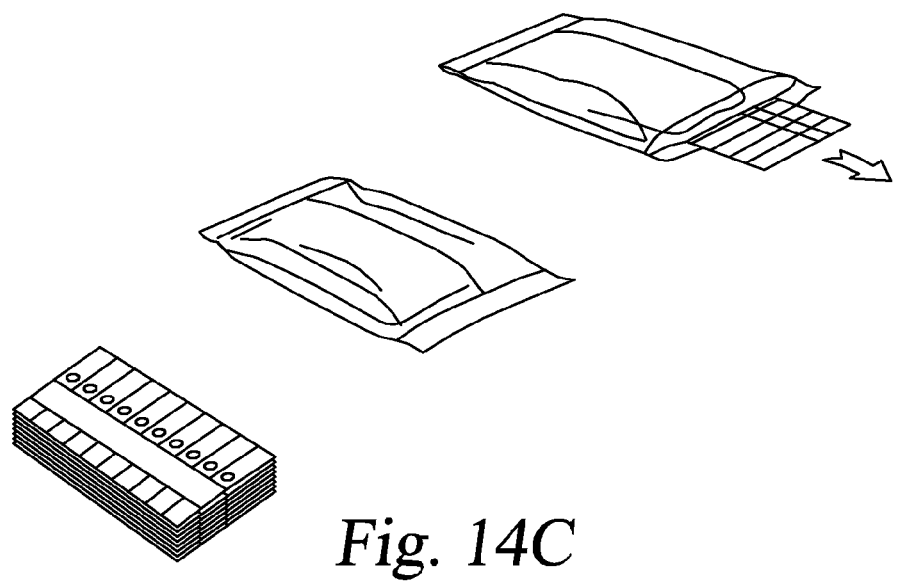
Figure 15A:
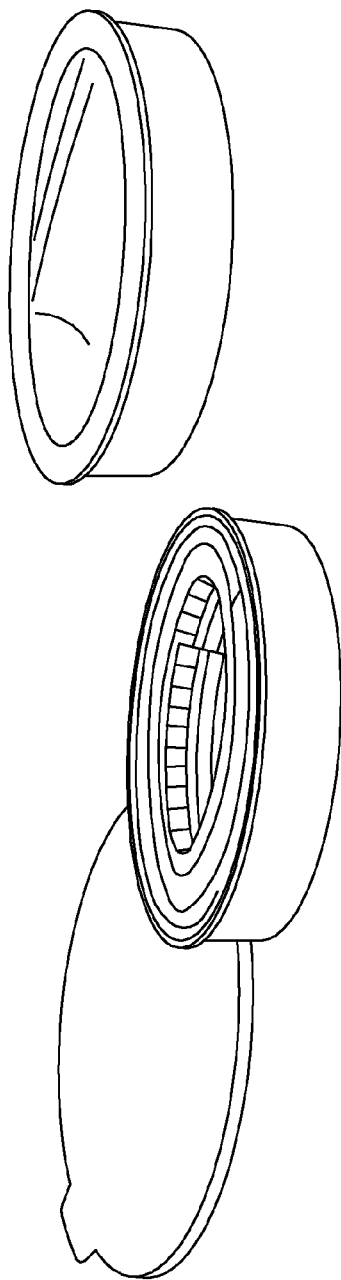
FIGS. 15A-C are perspective views of storage containers in the form of an aluminium can (FIG. 15A), of a TicTac® dispenser (FIG. 15B) and a plastic bag (FIG. 15C) which each contains a plurality of interconnected, individually separable test strips in a roll-shaped arrangement.
Figure 15B:
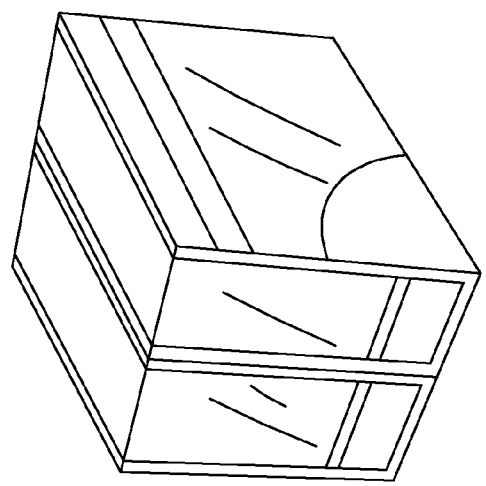
Figure 15C:
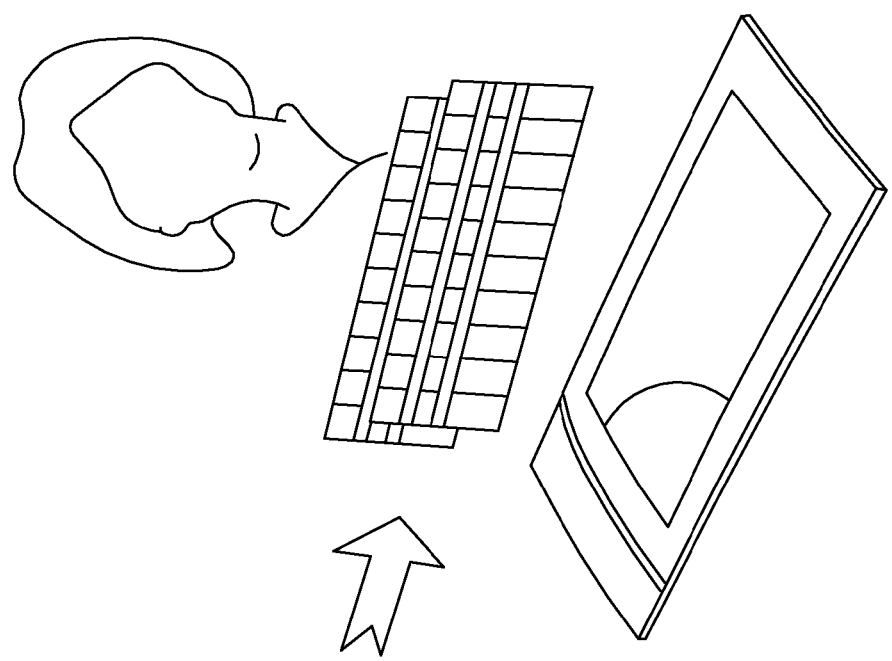
Figure 15C:
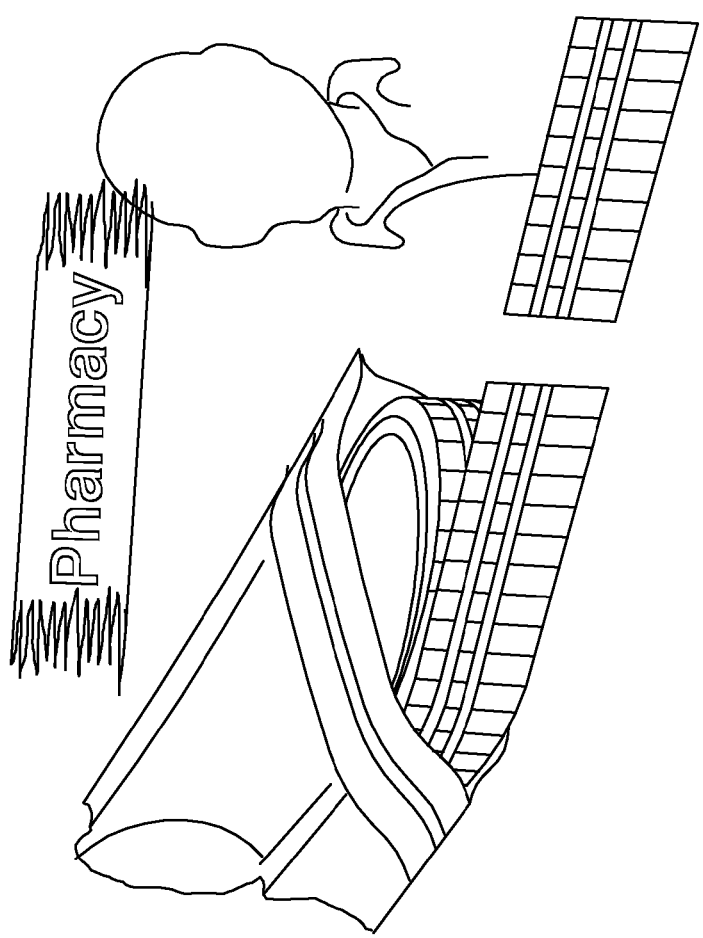
Figure 16:
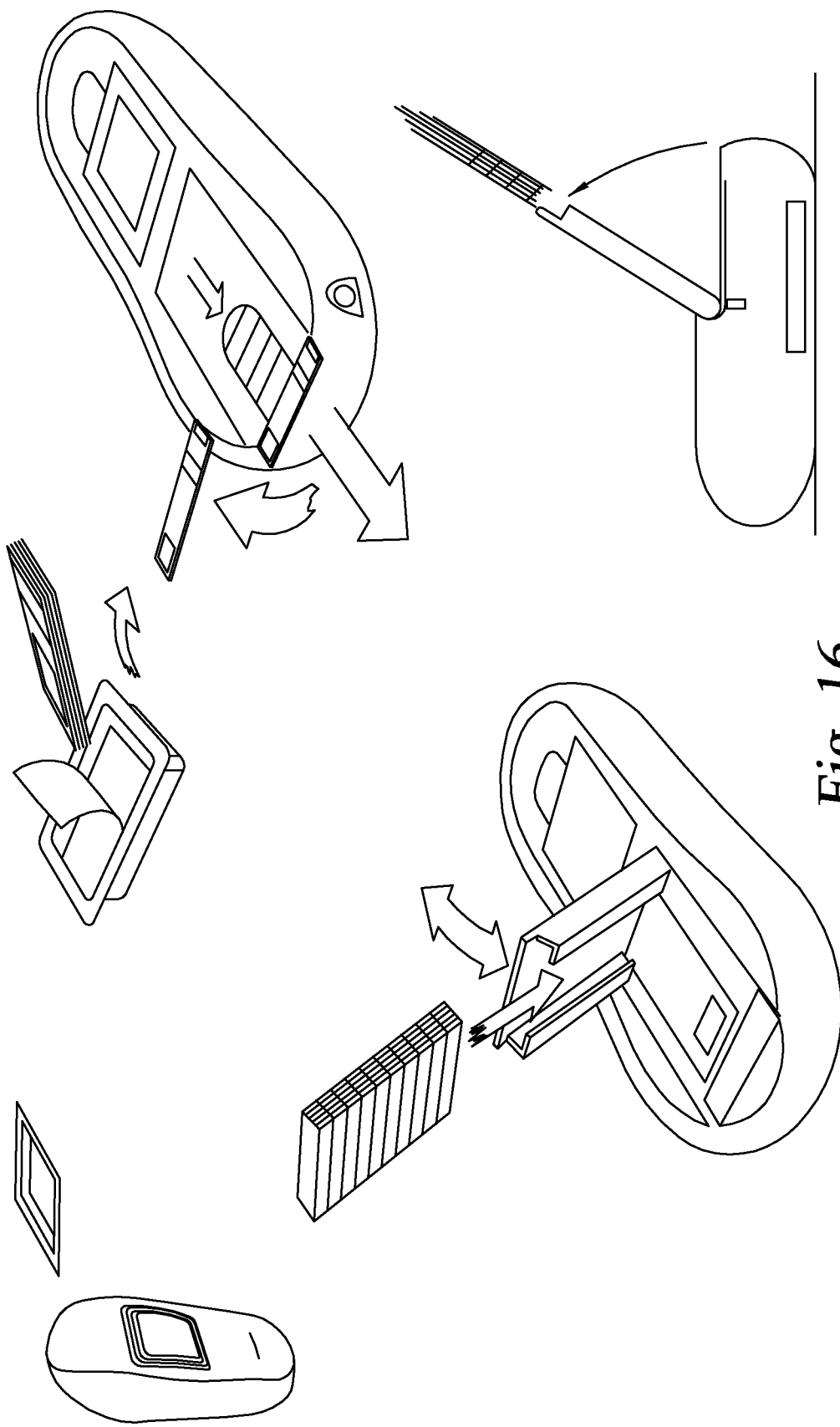
FIG. 16 is a schematic illustration of an analytical measuring device with an integrated storage container which contains a plurality of interconnected, individually separable test strips in a bar-shaped arrangement.

FIG. 11 shows an exemplary embodiment of a storage container in cross-section in the form of a disk-shaped turning magazine which can be inserted into an analytical measuring device 114. In this case the analytical measuring device 114 has a housing 112 with a finger opening 116 through which a sampling movement can take place.

The storage container 110 has two submagazines in the form of half magazines 172, 174 which are designed to be essentially symmetrical to one another. In particular, the storage container 110 comprises a housing 122 with a round middle opening 124 as well as two device planes 118, 120 which are each arranged in parallel above one another and extend parallel to the plane of the storage container. A plurality of chambers 126 are accommodated in each of the two device planes 118, 120 in the housing 122, where the chambers 126 of the second device plane 120 are each rotated by a half unit below the chambers 126 of the first device plane 118. Hence the storage container 110 can be composed of two identical half planes which are mounted against each other and are each rotated by half a unit against each other; i.e. by one half angular separation of the chambers 126.

Analytical devices 128 are accommodated in each of the chambers 126 which are in turn composed of several partial devices 130. The first partial device 130 comprises a microsampler 132 radially mounted in the chambers 126 which in turn comprises a lancet 134 and a capillary element 136 extending radially inwards from the lancets 134. The microsamplers 132 each have coupling elements 138 at their end pointing towards the middle opening 124, which can be designed in the form of eyes into which an actuator (not shown in FIG. 11) of the analytical measuring device 114 can engage in the middle opening 124 by means of a hook-shaped push rod or an actuator rod. The analytical devices 128 have a diagnostic test element 140 as a second partial device 130 which includes a test chemistry 142 in the form of a test area 144 and can be integrated into the housing 122.

The storage container 110 is designed such that the analytical devices 128 can be arranged offset to one another in the two device planes 118, 120. Accordingly, one test element window 168 of one of the two device planes 118, 120 is located in each case between two chambers 126 of the respective other device plane 118, 120. This ensures that the rear side of the test area 144 can be observed in its application position by means of the analytical measuring device undisturbed by neighbouring chambers 126 of the respective other device plane 118, 120. The displaced arrangement of the chambers 126 thus allows the respective active diagnostic test elements 140 to be accessed from both sides in their application position. The remaining analytical devices 128 in the storage container 110 are generally not exposed in this process and remain sterile until use due to their appropriate sealings.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A storage container, comprising:
 at least one diagnostic test element including a dry reagent layer comprising an enzyme and a stabilized coenzyme, wherein the storage container (a) is essentially free of desiccants and (b) comprises no sealing elements which substantially prevent penetration of moisture from an environment into the storage container, wherein the stabilized coenzyme stabilizes the enzyme, wherein the enzyme is a dehydrogenase, and wherein the stabilized coenzyme is a compound of general formula (I):

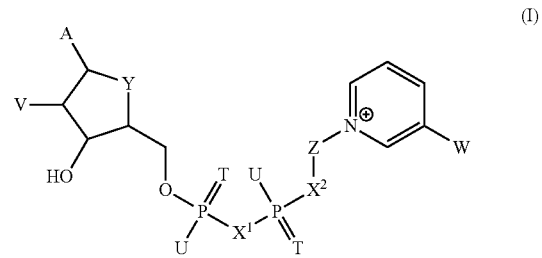

in which
A=adenine or an analogue thereof;
T=in each case independently denotes O or S;
U=in each case independently denotes OH, SH, $BH_3^-$, or $BCNH_2^-$;

V=in each case independently denotes OH or a phosphate group, or two groups which form a cyclic phosphate group;

W=COOR, CON(R)$_2$, COR, or CSN(R)$_2$ in which R in each case independently denotes H or a $C_1$-$C_2$ alkyl;

$X^1$, $X^2$=in each case independently denote O, $CH_2$, $CHCH_3$, $C(CH_3)_2$, NH, or $NCH_3$;

Y=NH, S, O, or $CH_2$;

Z=a linear residue or a cyclic organic residue, provided that Z and the pyridine residue are not linked by a glycosidic bond, or a salt or optionally a reduced form thereof.

2. The storage container of claim 1 wherein at least one of a minimum and a maximum pulling force required to transport one or more unused test areas of the at least one test element from a storage position within the storage container to at least one of a sample application position and a measuring position outside the storage container is reduced compared to a corresponding storage container with a sealing element.

3. The storage container of claim 1 wherein at least one of a minimum and a maximum pulling force required to transport one or more used test areas of the at least one test element from at least one of a sample application position and a measuring position outside the storage container to a storage position within the storage container is reduced compared to a corresponding storage container with a sealing element.

4. The storage container of claim 1, wherein the at least one test element comprises one or more test areas, and in each case an individual test area of the at least one test element can interact with an analytical measuring device.

5. The storage container of claim 1, further comprising a sample application position, a measuring position and at least one storage position for the at least one test element.

6. The storage container of claim 1, wherein the storage container is constructed from at least one material permeable to water vapour, and wherein the at least one material permeable to water vapour is a plastic selected from the group consisting of polyamide, polycarbonate, polyester, polyethylene and polypropylene.

7. The storage container of claim 1, further comprising one of a tape magazine and a test strip magazine.

8. The storage container of claim 1, further comprising one of a blister magazine, leporello magazine, disk magazine, stack magazine, drum magazine and turning magazine.

9. The storage container of claim 1, further comprising a plurality of entry openings, wherein one or more of the entry openings has a diameter of ≤100 μm.

10. The storage container of claim 9, wherein one or more of the entry openings has a diameter of ≤20 μm.

11. The storage container of claim 1, wherein the dehydrogenase is one of a nicotinamide adenine dinucleotide (NAD/NADH)-dependent dehydrogenase or a nicotinamide adenine dinucleotide phosphate (NADP/NADPH)-dependent dehydrogenase.

12. The storage container of claim 1, wherein the dehydrogenase is one of a glucose dehydrogenase (EC 1.1.1.47) and a glucose-6-phosphate dehydrogenase (EC 1.1.1.49).

13. The storage container of claim 1, wherein the stabilized coenzyme is a stabilized NAD(P)/NAD(P)H compound.

14. The storage container of claim 13, wherein the stabilized NAD(P)/NAD(P)H compound is carbaNAD.

15. The storage container of claim 1, wherein the at least one test element further comprises a mediator selected from the group consisting of a 1,10-phenanthroline quinone, a 1,7-phenanthroline quinone and a 4,7-phenanthroline quinone.

16. The storage container of claim 1, wherein the at least one test element is essentially free of desiccants.

17. The storage container of claim 1, wherein the at least one test element further comprises a needle element for making a small incision in the skin.

18. The storage container of claim 1, wherein the at least one test element is one of a test tape, a test disk, a test pad and a test strip.

19. The storage container of claim 18, wherein the at least one test element is a continuous test tape.

20. The storage container of claim 1, wherein the at least one test element exhibits a reduction of enzyme activity of less than one of 50%, 30%, and 20% compared to the initial value of enzyme activity after storage in the storage container for a period selected from the group consisting of at least one of 4 weeks, 8 weeks, and 12 weeks at a temperature of at least one of 20° C., 25° C. and 30° C.

21. The storage container of claim 1, further comprising a test strip magazine including a plurality of interconnected, individually separable test strips in one of a bar-shaped and a roll-shaped arrangement.

22. The storage container of claim 1, wherein the at least one test element is stable for a period of up to 5 weeks, for up to 32° C. and up to 85% air humidity.

* * * * *